United States Patent
Liard et al.

(10) Patent No.: US 11,931,449 B2
(45) Date of Patent: Mar. 19, 2024

(54) HAIR DYEING PROCESS USING AT LEAST ONE SILICONE COMPRISING AT LEAST ONE CARBOXYLIC ACID ANHYDRIDE GROUP, AT LEAST ONE AMINO SILICONE AND AT LEAST ONE PIGMENT AND/OR DIRECT DYE

(71) Applicant: L'OREAL, Paris (FR)

(72) Inventors: Alexis Liard, Saint-Ouen (FR); Chrystel Pourille, Saint-Ouen (FR)

(73) Assignee: L'OREAL, Paris (FR)

( * ) Notice: Subject to any disclaimer, the term of this patent is extended or adjusted under 35 U.S.C. 154(b) by 0 days.

(21) Appl. No.: 17/784,917

(22) PCT Filed: Nov. 24, 2020

(86) PCT No.: PCT/EP2020/083219
§ 371 (c)(1),
(2) Date: Jun. 13, 2022

(87) PCT Pub. No.: WO2021/121882
PCT Pub. Date: Jun. 24, 2021

(65) Prior Publication Data
US 2023/0040319 A1    Feb. 9, 2023

(30) Foreign Application Priority Data

Dec. 16, 2019  (FR) ...................... 1914534

(51) Int. Cl.
| | | |
|---|---|---|
| A61Q 5/10 | (2006.01) | |
| A61K 8/19 | (2006.01) | |
| A61K 8/894 | (2006.01) | |
| A61K 8/898 | (2006.01) | |

(52) U.S. Cl.
CPC ............... *A61K 8/898* (2013.01); *A61K 8/19* (2013.01); *A61K 8/894* (2013.01); *A61Q 5/10* (2013.01); *A61K 2800/43* (2013.01); *A61K 2800/594* (2013.01); *A61K 2800/884* (2013.01)

(58) Field of Classification Search
CPC .......... A61K 8/898; A61K 8/19; A61K 8/894; A61K 2800/43; A61K 2800/594; A61K 2800/884; A61K 2800/882; A61K 8/891; A61Q 5/10; A61Q 5/065
USPC .......................................................... 8/405
See application file for complete search history.

(56) References Cited

U.S. PATENT DOCUMENTS

| | | |
|---|---|---|
| 4,185,087 A | 1/1980 | Morlino |
| 4,578,266 A | 3/1986 | Tietjen et al. |
| 5,645,609 A | 7/1997 | Andrean et al. |
| 5,708,151 A | 1/1998 | Möckli |
| 5,990,479 A | 11/1999 | Weiss et al. |
| 6,225,198 B1 | 5/2001 | Alivisatos et al. |
| 11,253,459 B2 | 2/2022 | Seneca et al. |
| 2008/0269352 A1 | 10/2008 | Falkowski et al. |
| 2010/0183536 A1 | 7/2010 | Ansmann et al. |
| 2013/0129648 A1* | 5/2013 | Nguyen .................. A61Q 5/12 424/59 |
| 2015/0182441 A1* | 7/2015 | Goutsis .................. A61K 8/55 8/405 |
| 2020/0060960 A1 | 2/2020 | Seneca et al. |

FOREIGN PATENT DOCUMENTS

| | | |
|---|---|---|
| EP | 0530974 A1 | 3/1993 |
| EP | 0714954 A2 | 6/1996 |
| EP | 01184426 A2 | 3/2002 |
| FR | 2679771 A1 | 2/1993 |
| FR | 3066109 A1 | 11/2018 |
| FR | 3066110 A1 | 11/2018 |
| FR | 3066111 A1 | 11/2018 |
| FR | 3066112 A1 | 11/2018 |
| JP | 05-017710 A | 1/1993 |
| JP | 07-258460 A | 10/1995 |
| JP | 09-188830 A | 7/1997 |
| JP | 10-158450 A | 6/1998 |
| JP | 10-158541 A | 6/1998 |
| WO | 95/01772 A1 | 1/1995 |
| WO | 95/15144 A1 | 6/1995 |
| WO | 2007/068371 A1 | 6/2007 |
| WO | 2008/155059 A2 | 12/2008 |
| WO | 2018/206451 A1 | 11/2018 |
| WO | 2018/206457 A1 | 11/2018 |

OTHER PUBLICATIONS

STIC Search Report dated May 18, 2023.*
Dabbousi, B.O., et al., "(CdSe)ZnS Core-Shell Quantum Dots: Synthesis and Characterization of a Size Series of Highly Luminescent Nanocrystallites," Journal of Physical Chemistry B, vol. 101, 1997, pp. 9463-9475.
Peng, Xiaogang et al., "Epitaxial Growth of Highly Luminescent CdSe/CdS Core/Shell Nanocrystals with Photostability and Electronic Accessibility," Journal of the American Chemical Society, vol. 119, No. 30, 1997, pp. 7019-7029.
Schlossman, Mitchell L., "Treated Pigments New Ways to Impart Color on the Skin," Cosmetics and Toiletries, vol. 105, Feb. 1990, pp. 53-64.

\* cited by examiner

*Primary Examiner* — Eisa B Elhilo
(74) *Attorney, Agent, or Firm* — THE MARBURY LAW GROUP, PLLC

(57) ABSTRACT

The subject of the present invention is a process for treating keratin fibers using a) at least one silicone comprising at least one carboxylic acid anhydride group, b) at least one amino silicone, and c) at least one coloring agent chosen from pigments, direct dyes and mixtures thereof, the compounds a), b) and c) being applied together or separately, in one or more compositions.

15 Claims, No Drawings

HAIR DYEING PROCESS USING AT LEAST ONE SILICONE COMPRISING AT LEAST ONE CARBOXYLIC ACID ANHYDRIDE GROUP, AT LEAST ONE AMINO SILICONE AND AT LEAST ONE PIGMENT AND/OR DIRECT DYE

CROSS REFERENCE TO RELATED APPLICATION

This is a national stage application of PCT/EP2020/083219, filed internationally on Nov. 24, 2020, which claims priority to French Application No. 1914534, filed on Dec. 16, 2019, the contents of both of which are incorporated by reference herein in their entireties.

A subject of the present invention is thus a process for treating keratin fibers using a) at least one silicone comprising at least one carboxylic acid anhydride group, b) at least one amino silicone, and c) at least one coloring agent chosen from pigments, direct dyes and mixtures thereof, the compounds a), b) and c) being applied together or separately, in one or more compositions.

TECHNICAL FIELD

In the field of dyeing keratin fibers, in particular human keratin fibers, it is already known practice to dye keratin fibers via various techniques using direct dyes or pigments for non-permanent dyeing, or dye precursors for permanent dyeing.

There are essentially three types of process for dyeing the hair:

a) "permanent" dyeing, the function of which is to afford a substantial modification to the natural color and which uses oxidation dyes which penetrate into the hair fiber and forms the dye via an oxidative condensation process;

b) non-permanent, semi-permanent or direct dyeing, which does not use the oxidative condensation process and withstands four or five shampoo washes; it consists in dyeing keratin fibers with dye compositions containing direct dyes;

c) temporary dyeing, which gives rise to a modification of the natural color of the hair that remains from one shampoo washing to the next, and which serves to enhance or correct a shade that has already been obtained. It may also be likened to a "makeup" process.

For this last type of dyeing, it is known practice to use colored polymers formed by grafting one or more dyes of azo, triphenylmethane, azine, indoamine or anthraquinone nature onto a polymer chain. These colored polymers are not entirely satisfactory, notably as regards the homogeneity of the coloring obtained and its resistance, not to mention the problems associated with their manufacture and notably with their reproducibility.

Another dyeing method consists in using pigments. Specifically, the use of pigment on the surface of keratin fibers generally makes it possible to obtain visible colorings on dark hair, since the surface pigment masks the natural color of the fiber. However, the colorings obtained via this dyeing method have the drawback of having poor resistance to shampoo washing and also to external agents such as sebum, perspiration, blow-drying and/or rubbing.

In addition, compositions for temporarily dyeing the hair may also lead to a hair feel that is uncosmetic and/or not natural; the hair thus dyed may notably lack softness and/or suppleness and/or strand separation.

In addition, there are no effective makeup-removing compositions for removing this type of temporary dye composition when it is persistent with respect to shampoo washing.

The need thus remains for a process for treating keratin fibers, notably the hair, which has the advantage of obtaining a homogeneous and smooth colored coating on the hair, and also hair with complete strand separation, while at the same time forming a coating that is persistent with respect to shampoo washing and to the various attacking factors to which the hair may be subjected, such as blow-drying and/or rubbing, without degrading the hair. There is also a need to be able to eliminate this colored coating when so desired.

Thus, the aim of the present invention is to develop a process for treating keratin fibers, notably the hair, which has the advantage of obtaining a homogeneous and smooth colored coating on the hair, and also hair with complete strand separation, while at the same time forming a coating that is persistent with respect to shampoo washing and to the various attacking factors to which the hair may be subjected, such as blow-drying and/or rubbing, without degrading the hair. Advantageously, the colored coating can be readily eliminated when so desired.

DISCLOSURE OF THE INVENTION

The present invention relates to a process for treating keratin fibers such as the hair, using:
a) at least one silicone comprising at least one carboxylic acid anhydride group,
b) at least one amino silicone, and
c) at least one coloring agent chosen from pigments, direct dyes and mixtures thereof,
the compounds a), b) and c) being applied to the keratin fibers, together or separately, in one or more compositions.

The present invention also relates to a process for treating keratin fibers such as the hair, implementing:
a1) a step of treating said fibers by application to the keratin fibers of a composition (A) comprising b) at least one amino silicone;
b1) optionally a washing, rinsing, drying and/or wringing out step; and
c1) a step of treating by application to the keratin fibers of a composition (B) comprising a) at least one silicone comprising at least one carboxylic acid anhydride group;
the composition (A) and/or composition (B) optionally comprising c) at least one coloring agent chosen from pigments, direct dyes and mixtures thereof;
it being understood that steps a1), b1) and c1) are carried out successively a1), then b1) then c1) or else c1), then b1), then a1) or else steps a1) and c1) being carried out together followed by b1).

The present invention also relates to a multi-compartment device comprising:
a first compartment containing a composition (A) comprising b) at least one amino silicone;
a second compartment containing a composition (B) comprising a) at least one silicone comprising at least one carboxylic acid anhydride group;
and optionally a third compartment containing a makeup-removing composition (D) comprising at least one hydrocarbon-based oil;
the composition (A) and/or the composition (B) comprising c) at least one coloring agent chosen from pigments, direct dyes and mixtures thereof.

Through the use of this process, colored coatings are obtained on the hair that make it possible to obtain a coloring that is visible on all types of hair in a manner that is persistent with respect to shampoo washing, while at the same time preserving the physical qualities of the keratin fibers. Such a coating may be resistant to the external attacking factors to which the hair may be subjected, such as blow-drying and perspiration. It makes it possible in particular to obtain a smooth and uniform deposit.

Moreover, this composition makes it possible to obtain hair with complete strand separation, which can be styled without any problem.

The term "hair with strand separation" means hair which, after application of the composition and drying, is not stuck together (or of which all the strands are separated from each other) and thus does not form clumps of hair.

For the purposes of the present invention, the term "coloring that is persistent with respect to shampoo washing" means that the coloring obtained persists after one shampoo wash, preferably after three shampoo washes, more preferentially after five shampoo washes.

Advantageously, the colored coating thus obtained can be readily eliminated by means of a makeup-removing composition.

The term "at least one" means one or more.

Unless otherwise indicated, when the compounds are mentioned in the present patent application, this also includes the optical isomers thereof, the geometrical isomers thereof, the tautomers thereof, the salts thereof or the solvates thereof, alone or as a mixture.

The invention is not limited to the illustrated examples. The features of the various examples may notably be combined within variants which are not illustrated.

For the purposes of the present invention and unless otherwise indicated:
an "alkyl" radical denotes a linear or branched saturated radical containing, for example, from 1 to 20 carbon atoms;
an "aminoalkyl" radical denotes an alkyl radical as defined previously, said alkyl radical comprising an $NH_2$ group;
a "hydroxyalkyl" radical denotes an alkyl radical as defined previously, said alkyl radical comprising an OH group;
an "alkylene" radical denotes a linear or branched divalent saturated $C_1$-$C_4$ hydrocarbon-based group such as methylene, ethylene or propylene;
a "cycloalkyl" radical denotes a cyclic saturated hydrocarbon-based group comprising from 1 to 3 rings, preferably 2 rings, and comprising from 3 to 20 carbon atoms, preferably between 5 and 10 carbon atoms, such as cyclopentyl, cyclohexyl, cycloheptyl, norbornyl, or isobornyl, the cycloalkyl radical possibly being substituted with one or more ($C_1$-$C_4$)alkyl groups such as methyl; preferably, the cycloalkyl radical is an isobornyl group.
an "aryl" radical is a cyclic unsaturated aromatic radical comprising from 6 to 12 carbon atoms, which is mono- or bicyclic, fused or unfused; preferably, the aryl group comprises 1 ring containing 6 carbon atoms, such as phenyl;
an "aryloxy" radical denotes an aryl-oxy with "aryl" as defined previously;
an "alkoxy" radical denotes an "alkyl-oxy" radical with "alkyl" as defined previously;
an "acyloxy" radical denotes a radical R—COO with R being an alkyl group as defined previously.

The treatment process according to the invention is a process for dyeing keratin fibers such as the hair.

Preferably, the composition (A) and/or the composition (B) are compositions for treating keratin fibers such as the hair and more specifically compositions for dyeing keratin fibers such as the hair.

The term "keratin fibers" particularly means human keratin fibers such as head hair, eyelashes, eyebrows, and bodily hair, preferentially head hair, eyebrows and eyelashes, even more preferentially head hair.

Silicone Comprising a Carboxylic Anhydride Group:

The process according to the invention uses a composition comprising a) at least one silicone comprising at least one carboxylic acid anhydride group.

The term "carboxylic acid anhydride group" or "carboxylic anhydride group" is intended to mean a group of general formula R—CO—O—CO—R with R, which may be identical or different, independently representing an alkyl group containing from 1 to 6 carbon atoms, it being possible for the R groups to together form a ring.

The silicone(s) comprising at least one carboxylic acid anhydride group may be chosen from the organosiloxanes of formula (I) below:

[Chem. 1]

$$R_1-\underset{\underset{R_2}{|}}{\overset{\overset{R_2}{|}}{Si}}-O\left[\underset{\underset{R_2}{|}}{\overset{\overset{R_2}{|}}{Si}}-O\right]_m\left[\underset{\underset{R_1}{|}}{\overset{\overset{R_2}{|}}{Si}}-O\right]_n\underset{\underset{R_2}{|}}{\overset{\overset{R_2}{|}}{Si}}-R_1 \quad (I)$$

wherein:
$R_1$, which may be identical or different, independently represents an alkyl group containing from 1 to 20 carbon atoms, optionally substituted with at least one group chosen from a hydroxyl group (OH) or a thiol group (SH); a cycloalkyl group containing from 3 to 20 carbon atoms; an alkoxy group containing from 1 to 2 carbon atoms; an aryl group containing from 6 to 12 carbon atoms, optionally substituted with at least one group chosen from a hydroxyl group (OH) or a thiol group (SH) or a group of formula (II) below:

[Chem. 2]

$$(II)$$

wherein:
$R_3$ represents an alkyl group containing from 1 to 4 carbon atoms, and
p denotes an integer ranging from 0 to 4, preferably from 1 to 4,
$R_2$, which may be identical or different, independently represents an alkyl group containing from 1 to 20 carbon atoms, optionally substituted with at least one group chosen from a hydroxyl group (OH) or a thiol group (SH); a cycloalkyl group containing from 3 to 20 carbon atoms; an alkoxy group containing from 1 to 2 carbon atoms; an aryl group containing from 6 to 12 carbon atoms, optionally substituted with at least one group chosen from a hydroxyl group (OH) or a thiol group (SH);
m denotes an integer ranging from 1 to 10; and
n denotes an integer ranging from 1 to 50;
it being understood that at least one of the radicals $R_1$ represents a group of formula (II).

Preferably, the silicone(s) comprising at least one carboxylic acid anhydride group may be chosen from the organosiloxanes of formula (III) below:

[Chem. 3]

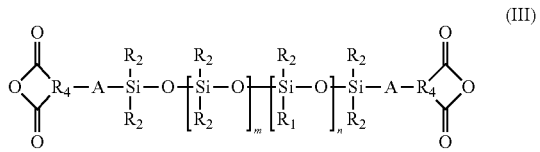

(III)

wherein:
$R_1$ independently represents an alkyl group containing from 1 to 20 carbon atoms, optionally substituted with at least one group chosen from a hydroxyl group (OH) or a thiol group (SH); a cycloalkyl group containing from 3 to 20 carbon atoms; an alkoxy group containing from 1 to 2 carbon atoms; an aryl group containing from 6 to 12 carbon atoms, optionally substituted with at least one group chosen from a hydroxyl group (OH) or a thiol group (SH) or a group of formula (II) below:

[Chem. 4]

(II)

wherein:
$R_3$ represents an alkyl group containing from 1 to 4 carbon atoms, and
p denotes an integer ranging from 0 to 4, preferably from 1 to 4,
$R_2$, which may be identical or different, independently represents an alkyl group containing from 1 to 20 carbon atoms, optionally substituted with at least one group chosen from a hydroxyl group (OH) or a thiol group (SH); a cycloalkyl group containing from 3 to 20 carbon atoms; an alkoxy group containing from 1 to 2 carbon atoms; an aryl group containing from 6 to 12 carbon atoms, optionally substituted with at least one group chosen from a hydroxyl group (OH) or a thiol group (SH);
$R_4$ represents an alkyl group containing from 1 to 4 carbon atoms;
A represents an alkylene group containing from 1 to 4 carbon atoms;
m denotes an integer ranging from 1 to 10; and
n denotes an integer ranging from 1 to 50.

Preferably, $R_1$ independently represents an alkyl group containing from 1 to 20 carbon atoms, more preferentially an alkyl group containing from 1 to 4 carbon atoms, and better still a methyl group.

Preferably, $R_1$, which may be identical or different, independently represents an alkyl group containing from 1 to 20 carbon atoms, more preferentially an alkyl group containing from 1 to 4 carbon atoms, and better still a methyl group.

Preferably, $R_4$ represents an alkyl group containing from 1 to 2 carbon atoms.

Preferably, A represents an alkylene group containing from 1 to 3 carbon atoms.

More preferentially, the silicone(s) comprising at least one carboxylic acid anhydride group may be chosen from the organosiloxanes of formula (IV) below:

[Chem. 5]

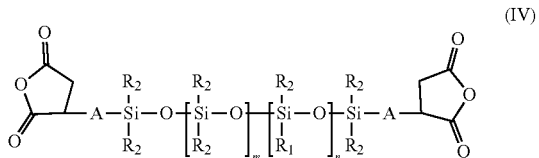

(IV)

wherein:
$R_2$, which may be identical or different, independently represents an alkyl group containing from 1 to 20 carbon atoms, optionally substituted with at least one group chosen from a hydroxyl group (OH) or a thiol group (SH); a cycloalkyl group containing from 3 to 20 carbon atoms; an alkoxy group containing from 1 to 2 carbon atoms; an aryl group containing from 6 to 12 carbon atoms, optionally substituted with at least one group chosen from a hydroxyl group (OH) or a thiol group (SH); preferably, $R_2$, which may be identical or different, independently represents an alkyl group containing from 1 to 20 carbon atoms, more preferentially an alkyl group containing from 1 to 4 carbon atoms, even more preferentially a methyl;
A represents an alkylene group containing from 1 to 4 carbon atoms, preferably from 1 to 3 carbon atoms;
m denotes an integer ranging from 1 to 10; and
n denotes an integer ranging from 1 to 50.

The weight-average molecular weight (Mw) of the silicone of formula (IV) preferably ranges from 200 to 50 000, even more particularly from 500 to 25 000 and more particularly from 500 to 15 000.

A silicone comprising at least one carboxylic acid anhydride group corresponding to formula (III) is for example the compound having the trade name X-22-168A sold by the company Shin Etsu.

A silicone comprising at least one carboxylic acid anhydride group corresponding to formula (IV) is for example the compound having the trade name DMS-Z21 (Cas Number 161205-23-8) sold by the company Gelest.

The composition(s) used in the process according to the invention may comprise one or more silicones comprising at least one carboxylic acid anhydride group, present in a total amount ranging from 0.1% to 40% by weight, preferably from 0.5% to 30% by weight, preferentially from 1% to 20% by weight and better still from 3% to 15% by weight, relative to the total weight of the composition.

Amino Silicone:
The process according to the invention uses a composition comprising b) at least one amino silicone.

The term "amino silicone" denotes any silicone including at least one primary, secondary or tertiary amine or a quaternary ammonium group.

The weight-average molecular weights of these amino silicones may be measured by gel permeation chromatography (GPC) at ambient temperature (25° C.), as polystyrene equivalent. The columns used are p styragel columns. The eluent is THF and the flow rate is 1 ml/minute. 200 μl of a 0.5% by weight solution of silicone in THF are injected. Detection is performed by refractometry and UV-metry.

Preferably, the amino silicone(s) that may be used in the context of the invention are chosen from:

a) the polysiloxanes corresponding to formula (A):

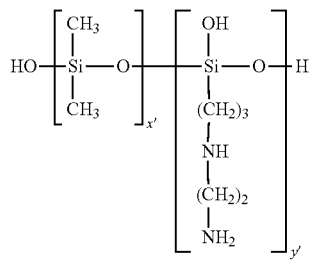
(A)

wherein x' and y' are integers such that the weight-average molecular weight (Mw) is between 5000 and 500 000 approximately.

b) the amino silicones corresponding to formula (B):

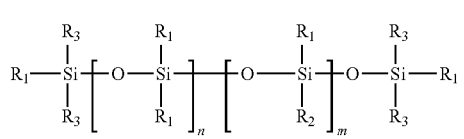
(B)

wherein:
$R_1$, which may be identical or different, represents a hydrogen atom, a phenyl group, a hydroxyl group, a $C_1$-$C_8$ alkyl group, for example a methyl, or a $C_1$-$C_6$ alkoxy group, for example methoxy;
$R_2$ represents a monovalent radical of formula —$C_qH_{2q}L$ wherein q is a number ranging from 2 to 8 and L is an optionally quaternized amino group chosen from the following groups:
—$N(R'')_2$; —$N^+(R'')_3A^-$; —$NR''$-Q-$N(R'')_2$ and —$NR''$-Q-$N^+(R'')_3A^-$,
wherein R", which may be identical or different, represents a hydrogen atom, a phenyl group, a benzyl group or a saturated monovalent hydrocarbon-based radical, for example a $C_1$-$C_{20}$ alkyl group; Q denotes a linear or branched group of formula $C_rH_{2r}$, r being an integer ranging from 2 to 6, preferably from 2 to 4; and $A^-$ represents a cosmetically acceptable anion, notably a halide such as fluoride, chloride, bromide or iodide;
$R_3$, which may be identical or different, represents a $C_1$-$C_8$ alkyl group, for example a methyl or a monovalent radical of formula —$C_qH_{2q}L$ wherein q is a number ranging from 2 to 11, and L is an optionally quaternized amino group chosen from the groups:
—$N(R'')_2$; —$N^+(R'')_3A^-$; —$NR''$-Q-$N(R'')_2$ and —$NR''$-Q-$N^+(R'')_3A^-$,
wherein R", which may be identical or different, represents a hydrogen atom, a phenyl group, a benzyl group or a saturated monovalent hydrocarbon-based radical, for example a $C_1$-$C_{20}$ alkyl group; Q denotes a linear or branched group of formula $C_rH_{2r}$, r being an integer ranging from 2 to 6, preferably from 2 to 4; and $A^-$ represents a cosmetically acceptable anion, notably a halide such as fluoride, chloride, bromide or iodide; and
m and n are numbers such that the sum (n+m) ranges from 1 to 2000 and in particular from 50 to 150, m possibly denoting a number from 0 to 1999 and notably from 49 to 149, and n possibly denoting a number from 1 to 2000 and notably from 1 to 10.

Preferably, the amino silicone(s) are chosen from the amino silicones of formula (B). Preferably, the amino silicone(s) of formula (B) are chosen from the amino silicones corresponding to the following formulae (C), (D), (E), (F) and/or (G).

Preferably, the amino silicone(s) of formula (B) are chosen from:

a) the "trimethylsilyl amodimethicone" silicones corresponding to formula (C):

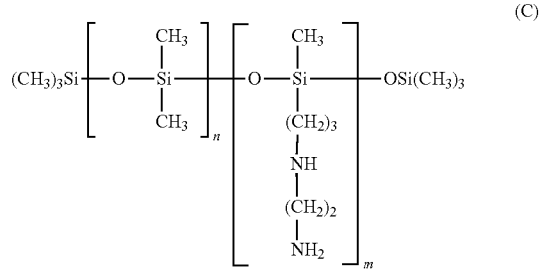
(C)

wherein m and n are numbers such that the sum (n+m) ranges from 1 to 2000.

A product containing amino silicones of structure (C) is provided by the company Shin Etsu under the name KF 8004 (INCI name: Amodimethicone).

b) the silicones of formula (D) below:

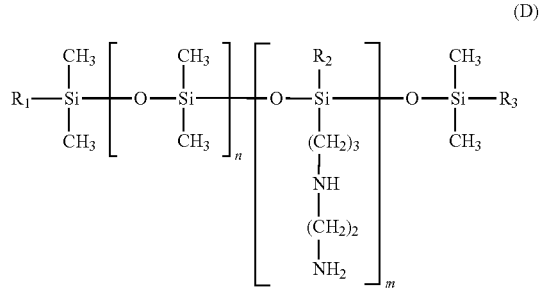
(D)

wherein:
m and n are numbers such that the sum (n+m) varies from 1 to 1000, notably from 50 to 250 and more particularly from 100 to 200, it being possible for n to denote a number from 0 to 999, in particular from 49 to 249 and more particularly from 125 to 175 and it being possible for m to denote a number from 1 to 1000, in particular from 1 to 10 and more particularly from 1 to 5;
$R_1$, $R_2$ and $R_3$, which may be identical or different, represent a hydroxyl or $C_1$-$C_4$ alkoxy radical, at least one of the radicals $R_1$ to $R_3$ denoting an alkoxy radical.

Preferably, the alkoxy radical is a methoxy radical.

The hydroxy/alkoxy mole ratio preferably ranges from 0.2:1 to 0.4:1, preferably from 0.25:1 to 0.35:1 and is more particularly equal to 0.3:1.

The weight-average molecular weight (Mw) of these silicones preferably ranges from 2000 to 1 000 000 and more particularly from 3500 to 200 000.

c) the silicones of formula (E) below:

[Chem. 10]

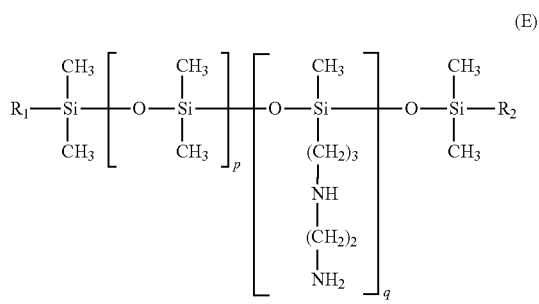

(E)

wherein:

p and q are numbers such that the sum (p+q) ranges from 1 to 1000, in particular from 50 to 350 and more particularly from 150 to 250; p possibly denoting a number from 0 to 999, notably from 49 to 349 and more particularly from 159 to 239, and q possibly denoting a number from 1 to 1000, notably from 1 to 10 and more particularly from 1 to 5;

$R_1$ and $R_2$, which are different, represent a hydroxyl or $C_1$-$C_4$ alkoxy radical, at least one of the radicals $R_1$ or $R_2$ denoting an alkoxy radical.

Preferably, the alkoxy radical is a methoxy radical.

The hydroxy/alkoxy mole ratio generally ranges from 1:0.8 to 1:1.1 and preferably from 1:0.9 to 1:1 and more particularly is equal to 1:0.95.

The weight-average molecular weight (Mw) of the silicone preferably ranges from 2000 to 200 000, even more particularly from 5000 to 100 000 and more particularly from 10 000 to 50 000.

The commercial products comprising silicones of structure (D) or (E) may include in their composition one or more other amino silicones of which the structure is different from formula (D) or (E).

A product containing amino silicones of structure (D) is sold by the company Wacker under the name Belsil® ADM 652.

A product containing amino silicones of structure (E) is sold by Wacker under the name Fluid WR 1300®.

When these amino silicones are used, one particularly advantageous embodiment consists in using them in the form of an oil-in-water emulsion. The oil-in-water emulsion may comprise one or more surfactants. The surfactants may be of any nature but are preferably cationic and/or nonionic. The number-mean size of the silicone particles in the emulsion generally ranges from 3 nm to 500 nanometers. Preferably, notably as amino silicones of formula (E), use is made of microemulsions with a mean particle size ranging from 5 nm to 60 nanometers (limits included) and more particularly from 10 nm to 50 nanometers (limits included). Thus, use may be made according to the invention of the amino silicone microemulsions of formula (E) sold under the names Finish CT 96 E® or SLM 28020® by the company Wacker.

d) the silicones of formula (F) below:

[Chem. 11]

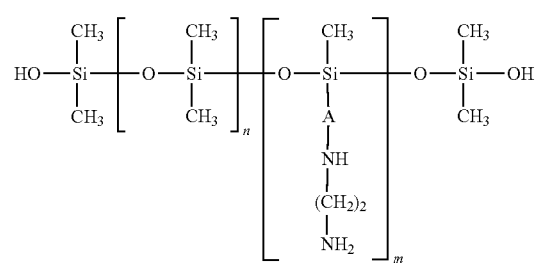

(F)

wherein:

m and n are numbers such that the sum (n+m) ranges from 1 to 2000 and in particular from 50 to 150, n possibly denoting a number from 0 to 1999 and notably from 49 to 149, and m possibly denoting a number from 1 to 2000 and notably from 1 to 10;

A denotes a linear or branched alkylene radical containing from 4 to 8 carbon atoms and preferably 4 carbon atoms. This radical is preferably linear.

The weight-average molecular weight (Mw) of these amino silicones preferably ranges from 2000 to 1 000 000 and even more particularly from 3500 to 200 000.

A silicone corresponding to this formula is, for example, the Xiameter MEM 8299 Emulsion from Dow Corning.

e) the silicones of formula (G) below:

[Chem. 12]

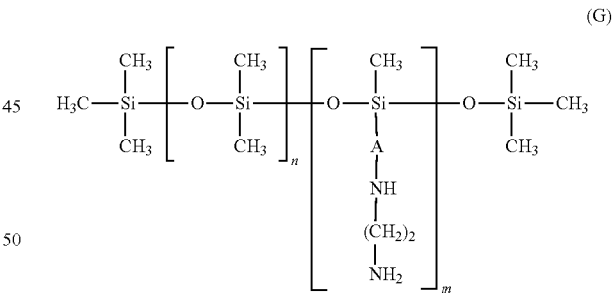

(G)

wherein:

m and n are numbers such that the sum (n+m) ranges from 1 to 2000 and in particular from 50 to 150, n possibly denoting a number from 0 to 1999 and notably from 49 to 149, and m possibly denoting a number from 1 to 2000 and notably from 1 to 10;

A denotes a linear or branched alkylene radical containing from 4 to 8 carbon atoms and preferably 4 carbon atoms. This radical is preferably branched.

The weight-average molecular weight (Mw) of these amino silicones preferably ranges from 500 to 1 000 000 and even more particularly from 1000 to 200 000.

A silicone corresponding to this formula is, for example, DC2-8566 Amino Fluid from Dow Corning;

f) the amino silicones corresponding to formula (H):

[Chem. 13]

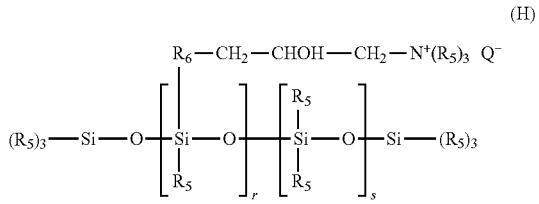

(H)

wherein:

$R_5$ represents a monovalent hydrocarbon-based radical containing from 1 to 18 carbon atoms, and in particular a $C_1$-$C_{18}$ alkyl or $C_2$-$C_{18}$ alkenyl, for example methyl, radical;

$R_6$ represents a divalent hydrocarbon-based radical, notably a $C_1$-$C_{18}$ alkylene radical or a divalent $C_1$-$C_{18}$, for example $C_1$-$C_8$, alkyleneoxy radical connected to the Si via an SiC bond;

$Q^-$ is an anion, such as a halide ion, in particular a chloride ion, or an organic acid salt, in particular an acetate;

r represents a mean statistical value ranging from 2 to 20 and in particular from 2 to 8;

s represents a mean statistical value ranging from 20 to 200 and in particular from 20 to 50.

Such amino silicones are notably described in U.S. Pat. No. 4,185,087.

i) the silicones comprising a quaternary ammonium, of formula (I):

[Chem. 14]

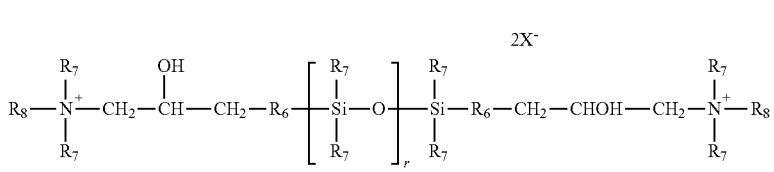

(I)

wherein:

$R_7$, which may be identical or different, represent a monovalent hydrocarbon-based radical containing from 1 to 18 carbon atoms, and in particular a $C_1$-$C_{18}$ alkyl radical, a $C_2$-$C_{18}$ alkenyl radical or a ring containing 5 or 6 carbon atoms, for example methyl;

$R_6$ represents a divalent hydrocarbon-based radical, notably a $C_1$-$C_{18}$ alkylene radical or a divalent $C_1$-$C_{18}$, for example $C_1$-$C_8$, alkyleneoxy radical linked to the Si via an SiC bond;

$R_8$, which may be identical or different, represent a hydrogen atom, a monovalent hydrocarbon-based radical containing from 1 to 18 carbon atoms, and in particular a $C_1$-$C_{18}$ alkyl radical, a $C_2$-$C_{18}$ alkenyl radical or a radical —$R_6$—NH-CO$R_7$;

$X^-$ is an anion, such as a halide ion, in particular a chloride ion, or an organic acid salt, in particular an acetate;

r represents a mean statistical value ranging from 2 to 200 and in particular from 5 to 100.

These silicones are described, for example, in patent application EP-A 0 530 974.

j) the amino silicones of formula (J):

[Chem. 15]

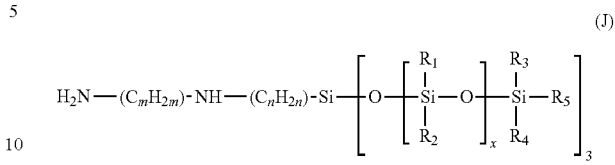

(J)

wherein:

$R_1$, $R_2$, $R_3$ and $R_4$, which may be identical or different, denote a $C_1$-$C_4$ alkyl radical or a phenyl group, $R_5$ denotes a $C_1$-$C_4$ alkyl radical or a hydroxyl group, n is an integer ranging from 1 to 5, m is an integer ranging from 1 to 5, and x is chosen such that the amine number ranges from 0.01 to 1 meq/g.

k) the multiblock polyoxyalkylenated amino silicones of the type (AB)n, A being a polysiloxane block and B being a polyoxyalkylene block including at least one amine group, Said silicones are preferably formed from repeating units having the following general formulae:

[Chem. 16]

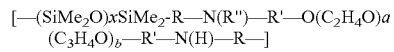

or alternatively

[Chem. 17]

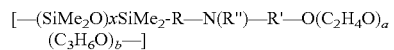

wherein:

a is an integer greater than or equal to 1, preferably ranging from 5 to 200 and more particularly ranging from 10 to 100;

b is an integer of between 0 and 200, preferably ranging from 4 to 100 and more particularly between 5 and 30;

x is an integer ranging from 1 to 10 000 and more particularly from 10 to 5000;

R" is a hydrogen atom or a methyl;

R, which may be identical or different, represent a linear or branched divalent $C_2$-$C_{12}$ hydrocarbon-based radical, optionally including one or more heteroatoms such as oxygen; preferably, R denotes an ethylene radical, a linear or branched propylene radical, a linear or branched butylene radical or a radical $CH_2CH_2CH_2OCH_2CH(OH)CH_2$—; preferentially, R denotes a radical $CH_2CH_2CH_2OCH_2CH(OH)CH_2$—;

R', which may be identical or different, represent a linear or branched divalent $C_2$-$C_{12}$ hydrocarbon-based radical, optionally including one or more heteroatoms such as oxygen; preferably, R' denotes an ethylene radical, a linear or branched propylene radical, a linear or branched butylene radical or a radical $CH_2CH_2CH_2OCH_2CH(OH)CH_2$—; preferentially, R' denotes —$CH(CH_3)$—$CH_2$—.

The siloxane blocks preferably represent from 50 mol % to 95 mol % of the total weight of the silicone, more particularly from 70 mol % to 85 mol %.

The amine content is preferably between 0.02 and 0.5 meq/g of copolymer in a 30% solution in dipropylene glycol, more particularly between 0.05 and 0.2.

The weight-average molecular weight (Mw) of the silicone is preferably between 5000 and 1 000 000 and more particularly between 10 000 and 200 000.

Mention may in particular be made of the silicones sold under the name Silsoft A-843 or Silsoft A—by Momentive.

1) and mixtures thereof.

Preferably, the amino silicone(s) according to the invention are chosen from the amino silicones of formula (C).

The composition(s) used in the process according to the invention preferably comprise(s) the amino silicone(s) in a total amount ranging from 0.01 to 20% by weight, preferably from 0.05 to 15% by weight and preferentially from 0.1 to 10% by weight, relative to the total weight of the composition.

Pigments and/or Direct Dye:

The process according to the invention uses a composition comprising c) at least one coloring agent chosen from pigments, direct dyes and mixtures thereof.

Preferably, the composition according to the invention comprises one or more pigments.

The term "pigment" is intended to mean any pigment that gives color to keratin materials. Their solubility in water at 25° C. and at atmospheric pressure (760 mmHg) is less than 0.05% by weight, and preferably less than 0.01%.

The pigments that may be used are notably chosen from the organic and/or mineral pigments known in the art, notably those described in Kirk-Othmer's Encyclopedia of Chemical Technology and in Ullmann's Encyclopedia of Industrial Chemistry.

They may be natural, of natural origin, or non-natural.

These pigments may be in pigment powder or paste form. They may be coated or uncoated.

The pigments may be chosen, for example, from mineral pigments, organic pigments, lakes, pigments with special effects such as nacres or glitter flakes, and mixtures thereof.

The pigment may be a mineral pigment. The term "mineral pigment" is intended to mean any pigment that satisfies the definition in Ullmann's encyclopedia in the chapter on inorganic pigments. Among the mineral pigments that are useful in the present invention, mention may be made of ochres such as red ochre (clay (in particular kaolinite) and iron hydroxide (for example hematite)), brown ochre (clay (in particular kaolinite) and limonite), yellow ochre (clay (in particular kaolinite) and goethite); titanium dioxide, optionally surface-treated; zirconium oxide or cerium oxide; zinc oxide, iron oxide (black, yellow or red) or chromium oxide; manganese violet, ultramarine blue, chromium hydrate and ferric blue; metal powders such as aluminum powder or copper powder.

Mention may also be made of carbonates of alkaline-earth metals (for example of calcium or magnesium), silicon dioxide, quartz, and also any other compound used as inert filler in cosmetic compositions, provided that these compounds afford the composition color or whiteness under the conditions in which they are used.

The pigment may be an organic pigment. The term "organic pigment" refers to any pigment that satisfies the definition in Ullmann's encyclopedia in the chapter on organic pigments.

The organic pigment may notably be chosen from nitroso, nitro, azo, xanthene, pyrene, quinoline, anthraquinone, triphenylmethane, fluorane, phthalocyanine, metal-complex, isoindolinone, isoindoline, quinacridone, perinone, perylene, diketopyrrolopyrrole, indigo, thioindigo, dioxazine, triphenylmethane and quinophthalone compounds.

Use may also be made of any mineral or organic compound that is insoluble in the composition that is conventional in the cosmetics field, provided that these compounds afford color or whiteness to the composition under the conditions under which they are used, for example guanine, which, according to the refractive index of the composition, is a pigment.

In particular, the white or colored organic pigments may be chosen from carmine, carbon black, aniline black, azo yellow, quinacridone, phthalocyanine blue, the blue pigments codified in the Color Index under the references CI 42090, 69800, 69825, 74100, 74160, the yellow pigments codified in the Color Index under the references CI 11680, 11710, 19140, 20040, 21100, 21108, 47000, 47005, the green pigments codified in the Color Index under the references CI 61565, 61570, 74260, the orange pigments codified in the Color Index under the references CI 11725, 45370, 71105, the red pigments codified in the Color Index under the references CI 12085, 12120, 12370, 12420, 12490, 14700, 15525, 15580, 15620, 15630, 15800, 15850, 15865, 15880, 26100, 45380, 45410, 58000, 73360, 73915, 75470, the pigments obtained by oxidative polymerization of indole or phenol derivatives as described in patent FR 2 679 771.

Examples that may also be mentioned include pigment pastes of organic pigments, such as the products sold by the company Hoechst under the names:

Cosmenyl Yellow IOG: Yellow 3 pigment (CI 11710);
Cosmenyl Yellow G: Yellow 1 pigment (CI 11680);
Cosmenyl Orange GR: Orange 43 pigment (CI 71105);
Cosmenyl Red R: Red 4 pigment (CI 12085);
Cosmenyl Carmine FB: Red 5 pigment (CI 12490);
Cosmenyl Violet RL: Violet 23 pigment (CI 51319);
Cosmenyl Blue A2R: Blue 15.1 pigment (CI 74160);
Cosmenyl Green GG: Green 7 pigment (CI 74260);
Cosmenyl Black R: Black 7 pigment (CI 77266).

The pigments in accordance with the invention may also be in the form of composite pigments, as described in patent EP 1 184 426. These composite pigments may be composed notably of particles including a mineral core, at least one binder, for attaching the organic pigments to the core, and at least one organic pigment which at least partially covers the core.

The organic pigment may also be a lake. The term "lake" refers to dyes adsorbed onto insoluble particles, the assembly thus obtained remaining insoluble during use.

The inorganic substrates onto which the dyes are adsorbed are, for example, alumina, silica, calcium sodium borosilicate, calcium aluminum borosilicate and aluminum.

Among the dyes, mention may be made of carminic acid. Mention may also be made of the dyes known under the following names: D&C Red 21 (CI 45 380), D&C Orange 5 (CI 45 370), D&C Red 27 (CI 45 410), D&C Orange 10 (CI 45 425), D&C Red 3 (CI 45 430), D&C Red 4 (CI 15 510), D&C Red 33 (CI 17 200), D&C Yellow 5 (CI 19 140), D&C Yellow 6 (CI 15 985), D&C Green (CI 61 570), D&C Yellow 1 O (CI 77 002), D&C Green 3 (CI 42 053), D&C Blue 1 (CI 42 090).

An example of a lake that may be mentioned is the product known under the following name: D&C Red 7 (CI 15 850:1).

The pigment may also be a pigment with special effects. The term "pigments with special effects" means pigments that generally create a colored appearance (characterized by a certain shade, a certain vivacity and a certain level of luminance) that is non-uniform and that changes as a function of the conditions of observation (light, temperature, angles of observation, etc.). They thereby differ from colored pigments, which afford a standard uniform opaque, semi-transparent or transparent shade.

Several types of pigments with special effects exist: those with a low refractive index, such as fluorescent or photochromic pigments, and those with a higher refractive index, such as nacres, interference pigments or glitter flakes.

Examples of pigments with special effects that may be mentioned include nacreous pigments such as mica coated with titanium or with bismuth oxychloride, colored nacreous pigments such as titanium mica with iron oxides, mica covered with iron oxide, titanium mica notably with ferric blue or with chromium oxide, titanium mica with an organic pigment of the abovementioned type, and also nacreous pigments based on bismuth oxychloride. Nacreous pigments that may be mentioned include the Cellini nacres sold by BASF (mica-TiO2-lake), Prestige Bronze sold by Eckart (mica-Fe2O3), and Colorona sold by Merck (mica-TiO2-Fe2O3).

Mention may also be made of the gold-colored nacres sold notably by the company BASF under the name Brilliant gold 212G (Timica), Gold 222C (Cloisonne), Sparkle gold (Timica), Gold 4504 (Chromalite) and Monarch gold 233X (Cloisonne); the bronze nacres sold notably by the company Merck under the name Bronze fine (17384) (Colorona) and Bronze (17353) (Colorona) and by the company BASF under the name Super bronze (Cloisonne); the orange nacres sold notably by the company BASF under the name Orange 363C (Cloisonne) and Orange MCR 101 (Cosmica) and by the company Merck under the name Passion orange (Colorona) and Matte orange (17449) (Microna); the brown nacres sold notably by the company BASF under the name Nu-antique copper 340XB (Cloisonne) and Brown CL4509 (Chromalite); the nacres with a copper tint sold notably by the company BASF under the name Copper 340A (Timica); the nacres with a red tint sold notably by the company Merck under the name Sienna fine (17386) (Colorona); the nacres with a yellow tint sold notably by the company BASF under the name Yellow (4502) (Chromalite); the red nacres with a gold tint sold notably by the company BASF under the name Sunstone G012 (Gemtone); the pink nacres sold notably by the company BASF under the name Tan opale G005 (Gemtone); the black nacres with a gold tint sold notably by the company BASF under the name Nu antique bronze 240 AB (Timica), the blue nacres sold notably by the company Merck under the name Matte blue (17433) (Microna), the white nacres with a silvery tint sold notably by the company Merck under the name Xirona Silver, and the golden-green pink-orange nacres sold notably by the company Merck under the name Indian summer (Xirona), and mixtures thereof.

Still as examples of nacres, mention may also be made of particles including a borosilicate substrate coated with titanium oxide.

Particles comprising a glass substrate coated with titanium oxide are notably sold under the name Metashine MC1080RY by the company Toyal.

Finally, examples of nacres that may also be mentioned include polyethylene terephthalate flakes, notably those sold by the company Meadowbrook Inventions under the name Silver 1P 0.004×0.004 (silver flakes). Multilayer pigments based on synthetic substrates such as alumina, silica, sodium calcium borosilicate or calcium aluminum borosilicate, and aluminum, may also be envisaged.

The pigments with special effects may also be chosen from reflective particles, i.e. notably from particles of which the size, structure, notably the thickness of the layer(s) of which they are made and their physical and chemical nature, and surface state, allow them to reflect incident light. This reflection may, where appropriate, have an intensity sufficient to create at the surface of the composition or of the mixture, when it is applied to the support to be made up, highlight points that are visible to the naked eye, i.e. more luminous points that contrast with their environment by appearing to sparkle.

The reflective particles may be selected so as not to significantly alter the coloring effect generated by the coloring agents with which they are combined, and more particularly so as to optimize this effect in terms of color rendition. They may more particularly have a yellow, pink, red, bronze, orange, brown, gold and/or coppery color or tint.

These particles may have varied forms and may notably be in platelet or globular form, in particular in spherical form.

Irrespective of their form, the reflective particles may or may not have a multilayer structure, and, in the case of a multilayer structure, may have, for example, at least one layer of uniform thickness, notably of a reflective material.

When the reflective particles do not have a multilayer structure, they may be composed, for example, of metal oxides, notably titanium or iron oxides obtained synthetically.

When the reflective particles have a multilayer structure, they may include, for example, a natural or synthetic substrate, notably a synthetic substrate at least partially coated with at least one layer of a reflective material, notably of at least one metal or metallic material. The substrate may be made of one or more organic and/or mineral materials.

More particularly, it may be chosen from glasses, ceramics, graphite, metal oxides, aluminas, silicas, silicates, notably aluminosilicates and borosilicates, and synthetic mica, and mixtures thereof, this list not being limiting.

The reflective material may include a layer of metal or of a metallic material.

Reflective particles are notably described in JP-A-09188830, JP-A-10158450, JP-A-10158541, JP-A-07258460 and JP-A-05017710.

Still as an example of reflective particles including a mineral substrate coated with a layer of metal, mention may also be made of particles including a silver-coated borosilicate substrate.

Particles with a silver-coated glass substrate, in the form of platelets, are sold under the name Microglass Metashine REFSX 2025 PS by the company Toyal. Particles with a glass substrate coated with nickel/chromium/molybdenum alloy are sold under the names Crystal Star GF 550 and GF 2525 by this same company.

Use may also be made of particles comprising a metallic substrate such as silver, aluminum, iron, chromium, nickel, molybdenum, gold, copper, zinc, tin, manganese, steel, bronze or titanium, said substrate being coated with at least one layer of at least one metal oxide such as titanium oxide, aluminum oxide, iron oxide, cerium oxide, chromium oxide or silicon oxides, and mixtures thereof.

Examples that may be mentioned include aluminum powder, bronze powder or copper powder coated with $SiO_2$ sold under the name Visionaire by the company Eckart.

Mention may also be made of pigments with an interference effect which are not attached to a substrate, such as liquid crystals (Helicones HC from Wacker) or interference holographic glitter flakes (Geometric Pigments or Spectra f/x from Spectratek). Pigments with special effects also comprise fluorescent pigments, whether these are substances that are fluorescent in daylight or that produce an ultraviolet fluorescence, phosphorescent pigments, photochromic pigments, thermochromic pigments and quantum dots, sold, for example, by the company Quantum Dots Corporation.

Quantum dots are luminescent semiconductor nanoparticles that are capable of emitting, under light excitation, radiation with a wavelength of between 400 nm and 700 nm. These nanoparticles are known from the literature. In particular, they may be synthesized according to the processes described, for example, in U.S. Pat. No. 6,225,198 or 5,990,479, in the publications cited therein and also in the following publications: Dabboussi B. O. et al., "(CdSe)ZnS core-shell quantum dots: synthesis and characterization of a size series of highly luminescent nanocrystallites", Journal of Physical Chemistry B, vol. 101, 1997, pages 9463-9475, and Peng, Xiaogang et al., "Epitaxial growth of highly luminescent CdSe/CdS core/shell nanocrystals with photostability and electronic accessibility", Journal of the American Chemical Society, vol. 119, No. 30, pages 7019-7029.

The variety of pigments that may be used in the present invention makes it possible to obtain a wide range of colors, and also particular optical effects such as metallic effects or interference effects.

The size of the pigment used in the composition according to the present invention is preferably between 10 nm and 200 μm, preferably between 20 nm and 80 μm, and more preferentially between 30 nm and 50 μm and even more preferentially between 80 nm and 10 μm.

The pigments may be dispersed in the composition by means of a dispersant.

The dispersant serves to protect the dispersed particles against their agglomeration or flocculation. This dispersant may be a surfactant, an oligomer, a polymer or a mixture of several thereof, bearing one or more functionalities with strong affinity for the surface of the particles to be dispersed. In particular, they may become physically or chemically attached to the surface of the pigments. These dispersants also contain at least one functional group that is compatible with or soluble in the continuous medium. In particular, 12-hydroxystearic acid esters and C8 to C20 fatty acid esters of polyols such as glycerol or diglycerol are used, such as poly(12-hydroxystearic) acid stearate with a molecular weight of about 750 g/mol, such as the product sold under the name Solsperse 21 000 by Avecia, polyglyceryl-2 dipolyhydroxystearate (CTFA name) sold under the reference Dehymyls PGPH by Henkel, or polyhydroxystearic acid such as the product sold under the reference Arlacel P100 by Uniqema, and mixtures thereof.

As other dispersants that may be used in the compositions of the invention, mention may be made of quaternary ammonium derivatives of polycondensed fatty acids, for instance Solsperse 17 000 sold by the company Avecia, and polydimethylsiloxane/oxypropylene mixtures such as those sold by the company Dow Corning under the references DC2-5185 and DC2-5225 C.

The pigments used in the composition may be surface-treated with an organic agent.

Thus, the pigments that have been surface-treated beforehand, which are useful in the context of the invention, are pigments that have totally or partially undergone a surface treatment of chemical, electronic, electrochemical, mechanochemical or mechanical nature, with an organic agent such as those described notably in Cosmetics and Toiletries, February 1990, Vol. 105, pages 53-64, before being dispersed in the composition in accordance with the invention. These organic agents may be chosen, for example, from waxes, for example carnauba wax and beeswax; fatty acids, fatty alcohols and derivatives thereof, such as stearic acid, hydroxystearic acid, stearyl alcohol, hydroxystearyl alcohol and lauric acid and derivatives thereof; anionic surfactants; lecithins; sodium, potassium, magnesium, iron, titanium, zinc or aluminum salts of fatty acids, for example aluminum stearate or laurate; metal alkoxides; polyethylene; (meth) acrylic polymers, for example polymethyl methacrylates; polymers and copolymers containing acrylate units; alkanolamines; silicone compounds, for example silicones, in particular polydimethylsiloxanes; organofluorine compounds, for example perfluoroalkyl ethers; fluorosilicone compounds.

The surface-treated pigments that are useful in the composition may also have been treated with a mixture of these compounds and/or may have undergone several surface treatments.

The surface-treated pigments that are useful in the context of the present invention may be prepared according to surface-treatment techniques that are well known to those skilled in the art, or may be commercially available as is.

Preferably, the surface-treated pigments are coated with an organic layer.

The organic agent with which the pigments are treated may be deposited on the pigments by solvent evaporation, chemical reaction between the molecules of the surface agent or creation of a covalent bond between the surface agent and the pigments.

The surface treatment may thus be performed, for example, by chemical reaction of a surface agent with the surface of the pigments and creation of a covalent bond between the surface agent and the pigments or the fillers. This method is notably described in U.S. Pat. No. 4,578,266.

An organic agent covalently bonded to the pigments will preferably be used.

The agent for the surface treatment may represent from 0.1% to 50% by weight relative to the total weight of the surface-treated pigment, preferably from 0.5% to 30% by weight and even more preferentially from 1% to 20% by weight relative to the total weight of the surface-treated pigment.

Preferably, the surface treatments of the pigments are chosen from the following treatments:

a PEG-silicone treatment, for instance the AQ surface treatment sold by LCW;

a methicone treatment, for instance the SI surface treatment sold by LCW;

a dimethicone treatment, for instance the Covasil 3.05 surface treatment sold by LCW;

a dimethicone/trimethyl siloxysilicate treatment, for instance the Covasil 4.05 surface treatment sold by LCW;

a magnesium myristate treatment, for instance the MM surface treatment sold by LCW;

an aluminum dimyristate treatment, such as the MI surface treatment sold by Miyoshi;

a perfluoropolymethylisopropyl ether treatment, for instance the FHC surface treatment sold by LCW;

an isostearyl sebacate treatment, for instance the HS surface treatment sold by Miyoshi;

a perfluoroalkyl phosphate treatment, for instance the PF surface treatment sold by Daito;

an acrylate/dimethicone copolymer and perfluoroalkyl phosphate treatment, for instance the FSA surface treatment sold by Daito;

a polymethylhydrogenosiloxane/perfluoroalkyl phosphate treatment, for instance the FS01 surface treatment sold by Daito;

an acrylate/dimethicone copolymer treatment, for instance the ASC surface treatment sold by Daito;

an isopropyl titanium triisostearate treatment, for instance the ITT surface treatment sold by Daito;

an acrylate copolymer treatment, for instance the APD surface treatment sold by Daito;

a perfluoroalkyl phosphate/isopropyl titanium triisostearate treatment, for instance the PF+ITT surface treatment sold by Daito.

According to a particular embodiment of the invention, the dispersant is present with organic or mineral pigments in submicron-sized particulate form in the composition according to the invention.

The term "submicron" or "submicronic" refers to pigments having a particle size that has been micronized by a micronization method and having a mean particle size of less than a micrometer (µm), in particular between 0.1 and 0.9 µm, and preferably between 0.2 and 0.6 µm.

According to one embodiment, the dispersant and the pigment(s) are present in an amount (dispersant:pigment) of between 1:4 and 4:1, particularly between 1.5:3 and 3:1.5 or better still between 1.7:2.5 and 2.5:1.7.

The dispersant(s) may therefore have a silicone backbone, such as silicone polyether and dispersants of amino silicone type other than the amino silicones as described previously.

Among the suitable dispersants, mention may be made of: amino silicones, i.e. silicones comprising one or more amino groups such as those sold under the names and references: BYK LPX 21879 by BYK, GP-4, GP-6, GP-344, GP-851, GP-965, GP-967 and GP-988-1, sold by Genesee Polymers, silicone acrylates such as Tego® RC 902, Tego® RC 922, Tego® RC 1041, and Tego® RC 1043, sold by Evonik, polydimethylsiloxane (PDMS) silicones with carboxyl groups such as X-22162 and X-22370 by Shin-Etsu, epoxy silicones such as GP-29, GP-32, GP-502, GP-504, GP-514, GP-607, GP-682, and GP-695 by Genesee Polymers, or Tego® RC 1401, Tego® RC 1403, Tego® RC 1412 by Evonik.

According to one particular embodiment, the dispersant(s) are of amino silicone type other than the amino silicones described previously and are cationic.

Preferably, the pigment(s) are chosen from mineral, mixed mineral-organic or organic pigments.

In one variant of the invention, the pigment(s) according to the invention are organic pigments, preferentially organic pigments surface-treated with an organic agent chosen from silicone compounds. In another variant of the invention, the pigment(s) according to the invention are mineral pigments.

The composition may comprise at least one direct dye.

The term "direct dye" means natural and/or synthetic dyes, other than oxidation dyes. These are dyes that will spread superficially on the fiber.

They may be ionic or nonionic, preferably anionic, cationic or nonionic.

Examples of suitable direct dyes that may be mentioned include azo direct dyes; (poly)methine dyes such as cyanines, hemicyanines and styryls; carbonyl dyes; azine dyes; nitro(hetero)aryl dyes; tri(hetero)arylmethane dyes; porphyrin dyes; phthalocyanine dyes and natural direct dyes, alone or in the form of mixtures.

The direct dyes may be chosen from cationic direct dyes. Mention may be made of the hydrazono cationic dyes of formulae (V) and (VI) and the azo cationic dyes (VII) and (VIII) below:

[Chem. 18]

$$\text{Het}^+\text{-C(Ra)}=\text{N}-\text{N(Rb)}-\text{Ar,Q} \qquad (V)$$

[Chem. 19]

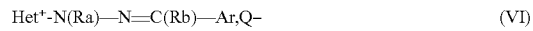

$$\text{Het}^+\text{-N(Ra)}-\text{N}=\text{C(Rb)}-\text{Ar,Q}- \qquad (VI)$$

[Chem. 20]

$$\text{Het}^+\text{-N}=\text{N-A,Q}- \qquad (VII)$$

[Chem. 21]

$$\text{Ar}^+\text{—N}=\text{N-A'',Q} \qquad (VIII)$$

formulae (V) to (VIII) wherein:

Het$^+$ represents a cationic heteroaryl radical, preferentially bearing an endocyclic cationic charge, such as imidazolium, indolium or pyridinium, which is optionally substituted, preferentially with at least one ($C_1$-$C_8$) alkyl group such as methyl;

Ar$^+$ represents an aryl radical, such as phenyl or naphthyl, bearing an exocyclic cationic charge, preferentially ammonium, particularly tri($C_1$-$C_8$)alkylammonium, such as trimethylammonium;

Ar represents an aryl group, notably phenyl, which is optionally substituted, preferentially with one or more electron-donating groups such as i) optionally substituted ($C_1$-$C_8$)alkyl, ii) optionally substituted ($C_1$-$C_8$)alkoxy, iii) (di)($C_1$-$C_8$)(alkyl)amino optionally substituted on the alkyl group(s) with a hydroxyl group, iv) aryl($C_1$-$C_8$)alkylamino, v) optionally substituted N—($C_1$-$C_8$)alkyl-N-aryl($C_1$-$C_8$)alkylamino or alternatively Ar represents a julolidine group;

Ar" represents an optionally substituted (hetero)aryl group, such as phenyl or pyrazolyl, which are optionally substituted, preferentially with one or more ($C_1$-$C_8$)alkyl, hydroxyl, (di)($C_1$-$C_8$)(alkyl)amino, ($C_1$-$C_8$)alkoxy or phenyl groups;

Ra and Rb, which may be identical or different, represent a hydrogen atom or a ($C_1$-$C_8$)alkyl group, which is optionally substituted, preferentially with a hydroxyl group; or else the substituent Ra with a substituent of Het+ and/or Rb with a substituent of Ar form, together with the atoms that bear them, a (hetero)cycloalkyl; in particular, Ra and Rb represent a hydrogen atom or a ($C_1$-$C_4$)alkyl group optionally substituted with a hydroxyl group;

Q$^-$ represents an organic or mineral anionic counterion, such as a halide or an alkyl sulfate.

In particular, mention may be made of the azo and hydrazono direct dyes bearing an endocyclic cationic charge of formulae (V) to (VIII) as defined previously. More particularly, the cationic direct dyes bearing an endocyclic cationic charge described in patent applications WO 95/15144, WO 95/01772 and EP 714 954. Preferentially the following direct dyes:

[Chem. 22]

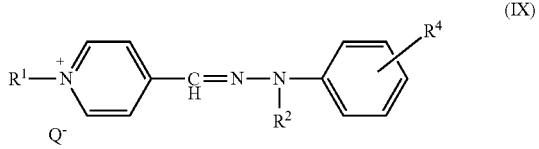

(IX)

[Chem. 23]

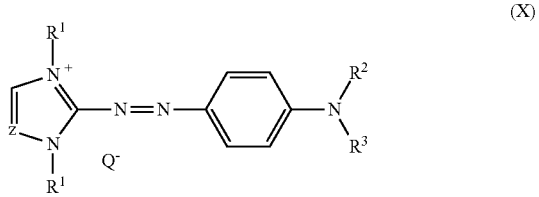

(X)

In particular, the dyes of formulae (IX) and (X) are chosen from Basic Red 51, Basic Yellow 87 and Basic Orange 31 or derivatives thereof with Q' being an anionic counterion as defined previously, particularly halide such as chloride, or an alkyl sulfate such as methyl sulfate or mesityl.

The direct dyes may be chosen from anionic direct dyes. The anionic direct dyes of the invention are dyes commonly referred to as "acid" direct dyes owing to their affinity for alkaline substances. The term "anionic direct dye" means any direct dye including in its structure at least one $CO_2R$ or $SO_3R$ substituent with R denoting a hydrogen atom or a cation originating from a metal or an amine, or an ammonium ion. The anionic dyes may be chosen from direct nitro acid dyes, azo acid dyes, azine acid dyes, triarylmethane acid dyes, indoamine acid dyes, anthraquinone acid dyes, indigoid dyes and natural acid dyes.

As acid dyes according to the invention, mention may be made of the dyes of formulae (XI), (XI'), (XII), (XII'), (XIII), (XIII'), (XIV), (XIV'), (XV), (XVI), (XVII) and (XVIII) below:

a) the diaryl anionic azo dyes of formula (XI) or (XI'):

[Chem. 24]

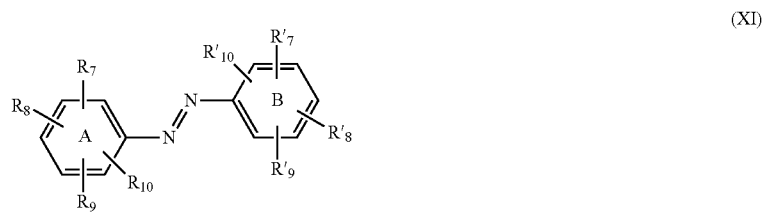

(XI)

[Chem. 25]

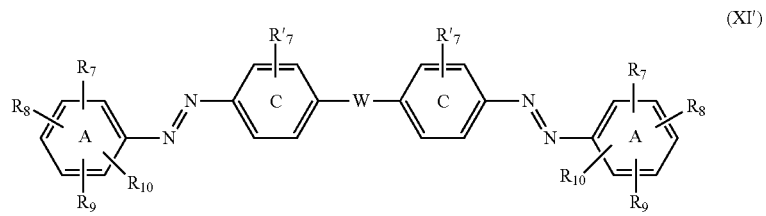

(XI')

formulae (IX) and (X) wherein:

$R^1$ represents a $(C_1-C_4)$alkyl group such as methyl;

$R^2$ and $R^3$, which may be identical or different, represent a hydrogen atom or a $(C_1-C_4)$alkyl group, such as methyl; and $R^4$ represents a hydrogen atom or an electron-donating group such as optionally substituted $(C_1-C_8)$alkyl, optionally substituted $(C_1-C_8)$alkoxy, or $(di)(C_1-C_8)(alkyl)amino$ optionally substituted on the alkyl group(s) with a hydroxyl group; particularly, $R^4$ is a hydrogen atom, Z represents a CH group or a nitrogen atom, preferentially CH, Q– is an anionic counterion as defined previously, in particular a halide, such as chloride, or an alkyl sulfate, such as methyl sulfate or mesityl.

formulae (XI) and (XI') wherein:

$R_7$, $R_8$, $R_9$, $R_{10}$, $R'_7$, $R'_8$, $R'_9$ and $R'_{10}$, which may be identical or different, represent a hydrogen atom or a group chosen from:

alkyl;

alkoxy, alkylthio;

hydroxyl, mercapto;

nitro, nitroso;

$R°$—C(X)—X'—, $R°$—X'—C(X)—, $R°$—X'—C(X)—X"— with $R°$ representing a hydrogen atom or an alkyl or aryl group; X, X' and X", which may be identical or different, representing an oxygen or sulfur atom, or NR with R representing a hydrogen atom or an alkyl group;

$(O)_2S(O^-)$—, $M^+$ with $M^+$ representing a hydrogen atom or a cationic counterion;

(O)CO⁻—, M⁺ with M⁺ as defined previously;

R″—S(O)₂—, with R″ representing a hydrogen atom or an alkyl, aryl, (di)(alkyl)amino or aryl(alkyl)amino group; preferentially a phenylamino or phenyl group;

R‴—S(O)₂—X′— with R‴ representing an optionally substituted alkyl or aryl group, X′ as defined previously;

(di)(alkyl)amino;

aryl(alkyl)amino optionally substituted with one or more groups chosen from i) nitro; ii) nitroso; iii) (O)₂S(O⁻)—, M⁺ and iv) alkoxy with M⁺ as defined previously;

optionally substituted heteroaryl; preferentially a benzothiazolyl group;

cycloalkyl; notably cyclohexyl;

Ar—N═N— with Ar representing an optionally substituted aryl group, preferentially a phenyl optionally substituted with one or more alkyl, (O)₂S(O⁻)—, M⁺ or phenylamino groups;

or alternatively two contiguous groups R₇ with R₈ or R₈ with R₉ or R₉ with R₁₀ together form a fused benzo group A'; and R'₇ with R'₈ or R'₈ with R'₉ or R'₉ with R'₁₀ together form a fused benzo group B'; with A' and B' optionally substituted with one or more groups chosen from i) nitro; ii) nitroso; iii) (O)₂S(O⁻)—, M⁺; iv) hydroxyl; v) mercapto; vi) (di)(alkyl)amino; vii) R°—C(X)—X'—; viii) R°—X'—C(X)—; ix) R°—X'—C(X)—X″—; x) Ar—N═N— and xi) optionally substituted aryl(alkyl)amino; with M⁺, R°, X, X', X″ and Ar as defined previously;

W represents a sigma bond σ, an oxygen or sulfur atom, or a divalent radical i) —NR— with R as defined previously, or ii) methylene —C(Ra)(Rb)— with Ra and Rb, which may be identical or different, representing a hydrogen atom or an aryl group, or alternatively Ra and Rb form, with the carbon atom that bears them, a spiro cycloalkyl; preferentially, W represents a sulfur atom or Ra and Rb together form a cyclohexyl;

it being understood that formulae (XI) and (XI') comprise at least one sulfonate radical (O)₂S(O⁻)—, M⁺ or one carboxylate radical (O)CO⁻—, M⁺ on one of the rings A, A', B, B' or C; preferentially sodium sulfonate.

As examples of dyes of formula (XI), mention may be made of: Acid Red 1, Acid Red 4, Acid Red 13, Acid Red 14, Acid Red 18, Acid Red 27, Acid Red 28, Acid Red 32, Acid Red 33, Acid Red 35, Acid Red 37, Acid Red 40, Acid Red 41, Acid Red 42, Acid Red 44, Pigment red 57, Acid Red 68, Acid Red 73, Acid Red 135, Acid Red 138, Acid Red 184, Food Red 1, Food Red 13, Acid Orange 6, Acid Orange 7, Acid Orange 10, Acid Orange 19, Acid Orange 20, Acid Orange 24, Yellow 6, Acid Yellow 9, Acid Yellow 36, Acid Yellow 199, Food Yellow 3, Acid Violet 7, Acid Violet 14, Acid Blue 113, Acid Blue 117, Acid Black 1, Acid Brown 4, Acid Brown 20, Acid Black 26, Acid Black 52, Food Black 1, Food Black 2, Food Yellow 3 or Sunset Yellow;

and, as examples of dyes of formula (XI'), mention may be made of: Acid Red 111, Acid Red 134, Acid yellow 38;

b) the pyrazolone anionic azo dyes of formulae (XII) and (XII'):

[00209]

[Chem. 26]

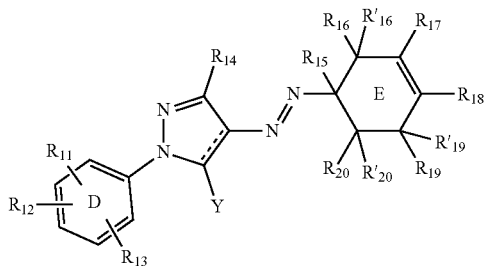

(XII)

[00210]

[Chem. 27]

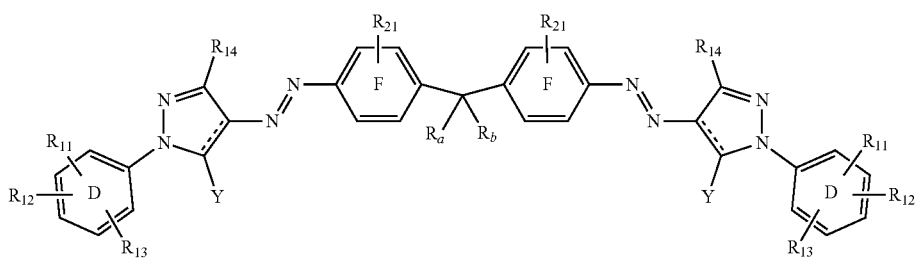

(XII')

formulae (XII) and (XII') wherein:

R₁₁, R₁₂ and R₁₃, which may be identical or different, represent a hydrogen or halogen atom, an alkyl group or —(O)₂S(O⁻), M⁺ with M⁺ as defined previously;

R₁₄ represents a hydrogen atom, an alkyl group or a group —C(O)O⁻, M⁺ with M⁺ as defined previously;

R₁₅ represents a hydrogen atom;

R₁₆ represents an oxo group, in which case R'₁₆ is absent, or alternatively R₁₅ with R₁₆ together form a double bond;

R₁₇ and R₁₈, which may be identical or different, represent a hydrogen atom, or a group chosen from:

(O)₂S(O⁻)—, M⁺ with M⁺ as defined previously;

Ar—O—S(O)$_2$— with Ar representing an optionally substituted aryl group; preferentially a phenyl optionally substituted with one or more alkyl groups;

R$_{19}$ and R$_{20}$ together form either a double bond, or a benzo group D', which is optionally substituted;

R'$_{16}$, R'$_{19}$ and R'$_{20}$, which may be identical or different, represent a hydrogen atom or an alkyl or hydroxyl group;

R$_{21}$ represents a hydrogen atom or an alkyl or alkoxy group;

R$_a$ and R$_b$, which may be identical or different, are as defined previously, preferentially R$_a$ represents a hydrogen atom and R$_b$ represents an aryl group;

Y represents either a hydroxyl group or an oxo group;

- - - - represents a single bond when Y is an oxo group; and represents a double bond when Y represents a hydroxyl group;

it being understood that formulae (XII) and (XII') comprise at least one sulfonate radical (O)$_2$S(O$^-$)—, M$^+$ or one carboxylate radical —C(O)O$^-$, M$^+$ on one of the rings D or E; preferentially sodium sulfonate.

As examples of dyes of formula (XII), mention may be made of: Acid Red 195, Acid Yellow 23, Acid Yellow 27, Acid Yellow 76, and as examples of dyes of formula (XII'), mention may be made of: Acid Yellow 17;

c) the anthraquinone dyes of formulae (XIII) and (XIII'):

[Chem. 28]

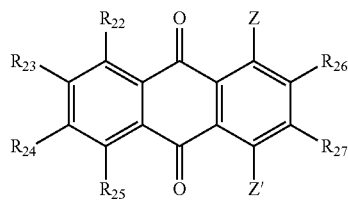

(XIII)

[Chem. 29]

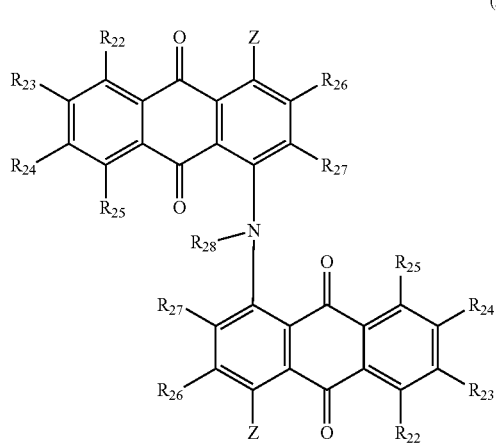

(XIII')

formulae (XIII) and (XIII') wherein:

R$_{22}$, R$_{23}$, R$_{24}$, R$_{25}$, R$_{26}$ and R$_{27}$, which may be identical or different, represent a hydrogen or halogen atom, or a group chosen from:
alkyl;
hydroxyl, mercapto;
alkoxy, alkylthio;
optionally substituted aryloxy or arylthio, preferentially substituted with one or more groups chosen from alkyl and (O)$_2$S(O$^-$)—, M$^+$ with M$^+$ as defined previously;

aryl(alkyl)amino optionally substituted with one or more groups chosen from alkyl and (O)$_2$S(O$^-$)—, M$^+$ with M$^+$ as defined previously;
(di)(alkyl)amino;
(di)(hydroxyalkyl)amino;
(O)$_2$S(O$^-$)—, M$^+$ with M$^+$ as defined previously;

Z' represents a hydrogen atom or a group NR28R29 with R28 and R29, which may be identical or different, representing a hydrogen atom or a group chosen from:
alkyl;
polyhydroxyalkyl such as hydroxyethyl;
aryl optionally substituted with one or more groups, particularly i) alkyl such as methyl, n-dodecyl, n-butyl; ii) (O)$_2$S(O$^-$)—, M$^+$ with M$^+$ as defined previously; iii) R$^\circ$—C(X)—X'—, R$^\circ$—X'—C(X)—, R$^\circ$—X'—C(X)—X"— with R$^\circ$, X, X' and X" as defined previously, preferentially R$^\circ$ represents an alkyl group;
cycloalkyl; notably cyclohexyl;

Z, represents a group chosen from hydroxyl and NR'28R'29 with R'28 and R'29, which may be identical or different, representing the same atoms or groups as R28 and R29 as defined previously;

it being understood that formulae (XIII) and (XIII') comprise at least one sulfonate radical (O)$_2$S(O$^-$)—, M$^+$ or one carboxylate radical —C(O)O$^-$, M$^+$; preferentially sodium sulfonate.

As examples of dyes of formula (XIII), mention may be made of Acid Blue 25, Acid Blue 43, Acid Blue 62, Acid Blue 78, Acid Blue 129, Acid Blue 138, Acid Blue 140, Acid Blue 251, Acid Green 25, Acid Green 41, Acid Violet 42, Acid Violet 43, Mordant Red 3; EXT violet No. 2; and, as an example of a dye of formula (XIII'), mention may be made of: Acid Black 48;

d) the nitro dyes of formulae (XIV) and (XIV'):

[Chem. 30]

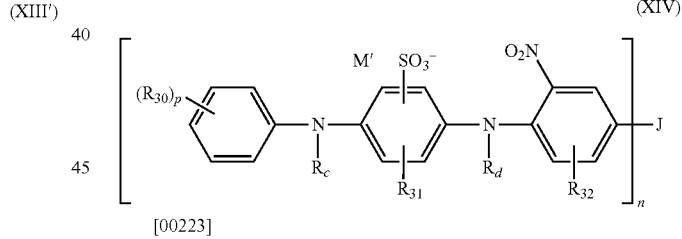

(XIV)

[00223]

[Chem. 31]

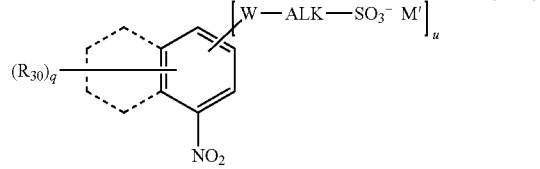

(XIV')

in which formulae (XIV) and (XIV'):

R$_{30}$, R$_{31}$ and R$_{32}$, which may be identical or different, represent a hydrogen or halogen atom, or a group chosen from:
alkyl;
alkoxy optionally substituted with one or more hydroxyl groups, alkylthio optionally substituted with one or more hydroxyl groups;
hydroxyl, mercapto;

nitro, nitroso;
polyhaloalkyl;
R°—C(X)—X'—, R°—X'—C(X)—, R°—X'—C(X)—X"— with R°, X, X' and X" as defined previously;
$(O)_2S(O^-)$—, $M^+$ with $M^+$ as defined previously;
$(O)CO^-$—, $M^+$ with $M^+$ as defined previously;
(di)(alkyl)amino;
(di)(hydroxyalkyl)amino;
heterocycloalkyl such as piperidino, piperazino or morpholino; in particular, $R_{30}$, $R_{31}$ and $R_{32}$ represent a hydrogen atom;
Rc and Rd, which may be identical or different, represent a hydrogen atom or an alkyl group;
W is as defined previously; W particularly represents an —NH— group;
ALK represents a linear or branched divalent $C_1$-$C_6$ alkylene group; in particular, ALK represents a —$CH_2$—$CH_2$— group;
n is 1 or 2;
p represents an integer inclusively between 1 and 5;
q represents an integer inclusively between 1 and 4;
u is 0 or 1;
when n is 1, J represents a nitro or nitroso group; particularly nitro;
when n is 2, J represents an oxygen or sulfur atom, or a divalent radical —$S(O)_m$— with m representing an integer 1 or 2; preferentially, J represents an —$SO_2$— radical;
M represents a hydrogen atom or a cationic counterion;

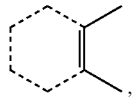

which may be present or absent, represents a benzo group optionally substituted with one or more groups R30 as defined previously;
it being understood that formulae (XIV) and (XIV') comprise at least one sulfonate radical $(O)_2S(O^-)$—, $M^+$ or one carboxylate radical $C(O)O^-$, $M^+$; preferentially sodium sulfonate.
As examples of dyes of formula (XIV), mention may be made of Acid Brown 13 and Acid Orange 3; as examples of dyes of formula (XIV'), mention may be made of Acid Yellow 1, the sodium salt of 2,4-dinitro-1-naphthol-7-sulfonic acid, 2-piperidino-5-nitrobenzenesulfonic acid, 2-(4'-N,N-(2"-hydroxyethyl)amino-2'-nitro)anilineethanesulfonic acid, 4-β-hydroxyethylamino-3-nitrobenzenesulfonic acid; EXT D&C Yellow 7;
e) the triarylmethane dyes of formula (XV):

[Chem. 32]

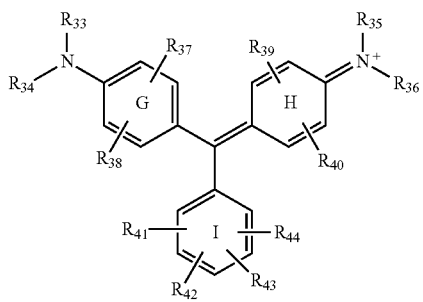

(XV)

formula (XV) wherein:
$R_{33}$, $R_{34}$, $R_{35}$ and $R_{36}$, which may be identical or different, represent a hydrogen atom or a group chosen from alkyl, optionally substituted aryl and optionally substituted arylalkyl; particularly an alkyl and benzyl group optionally substituted with a group $(O)_mS(O^-)$—, $M^+$ with $M^+$ and m as defined previously;
$R_{37}$, $R_{38}$, $R_{39}$, $R_{40}$, $R_{41}$, $R_{42}$, $R_{43}$ and $R_{44}$, which may be identical or different, represent a hydrogen atom or a group chosen from:
alkyl;
alkoxy, alkylthio;
(di)(alkyl)amino;
hydroxyl, mercapto;
nitro, nitroso;
R°—C(X)—X'—, R°—X'—C(X)—, R°—X'—C(X)—X"— with R° representing a hydrogen atom or an alkyl or aryl group; X, X' and X", which may be identical or different, representing an oxygen or sulfur atom, or NR with R representing a hydrogen atom or an alkyl group;
$(O)_2S(O^-)$—, $M^+$ with $M^+$ representing a hydrogen atom or a cationic counterion;
$(O)CO^-$—, $M^+$ with $M^+$ as defined previously;
or alternatively two contiguous groups $R_{41}$ with $R_{42}$ or $R_{42}$ with $R_{43}$ or $R_{43}$ with $R_{44}$ together form a fused benzo group: I'; with I' optionally substituted with one or more groups chosen from i) nitro; ii) nitroso; iii) $(O)_2S(O^-)$—, $M^+$; iv) hydroxyl; v) mercapto; vi) (di)(alkyl)amino; vii) R°—C(X)—X'—; viii) R°—X'—C(X)— and ix) R°—X'—C(X)—X"—; with $M^+$, R°, X, X' and X" as defined previously;
in particular, $R_{37}$ to $R_{40}$ represent a hydrogen atom, and $R_{41}$ to $R_{44}$, which may be identical or different, represent a hydroxyl group or $(O)_2S(O^-)$—, $M^+$; and when $R_{43}$ with $R_{44}$ together form a benzo group, it is preferentially substituted with an $(O)_2S(O^-)$— group;
it being understood that at least one of the rings G, H, I or I' comprises at least one sulfonate radical $(O)_2S(O^-)$— or a carboxylate radical —C(O)O—; preferentially sulfonate.
As examples of dyes of formula (XV), mention may be made of Acid Blue 1; Acid Blue 3; Acid Blue 7, Acid Blue 9; Acid Violet 49; Acid Green 3; Acid Green 5 and Acid Green 50;
e) the xanthene-based dyes of formula (XVI):

[Chem. 33]

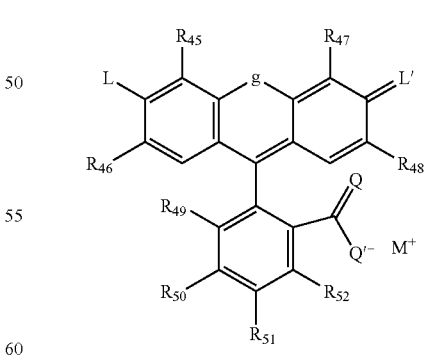

(XVI)

formula (XVI) wherein:
$R_{45}$, $R_{46}$, $R_{47}$ and $R_{48}$, which may be identical or different, represent a hydrogen or halogen atom;
$R_{49}$, $R_{50}$, $R_{51}$ and $R_{52}$, which may be identical or different, represent a hydrogen or halogen atom, or a group chosen from:

alkyl;
alkoxy, alkylthio;
hydroxyl, mercapto;
nitro, nitroso;
$(O)_2S(O^-)$—, $M^+$ with $M^+$ representing a hydrogen atom or a cationic counterion;
$(O)CO^-$—, $M^+$ with $M^+$ as defined previously;
particularly, $R_{53}$, $R_{54}$, $R_{55}$ and $R_{48}$ represent a hydrogen or halogen atom;

G represents an oxygen or sulfur atom or a group NRe with Re as defined previously; particularly G represents an oxygen atom;

L represents an alkoxide $O^-$, $M^+$; a thioalkoxide $S^-$, $M^+$ or a group NRf, with Rf representing a hydrogen atom or an alkyl group, and $M^+$ as defined previously; $M^+$ is particularly sodium or potassium;

L' represents an oxygen or sulfur atom or an ammonium group: $N^+RfRg$, with Rf and Rg, which may be identical or different, representing a hydrogen atom or an optionally substituted alkyl or aryl group; L' particularly represents an oxygen atom or a phenylamino group optionally substituted with one or more alkyl or $(O)_mS(O^-)$—, $M^+$ groups with m and $M^+$ as defined previously;

Q and Q', which may be identical or different, represent an oxygen or sulfur atom; in particular, Q and Q' represent an oxygen atom;

$M^+$ is as defined previously.

As an example of dyes of formula (XVI), mention may be made of: Acid Yellow 73; Acid Red 51; Acid Red 52; Acid Red 87; Acid Red 92; Acid Red 95; Acid Violet 9;

f) the indole-based dyes of formula (XVII):

[Chem. 34]

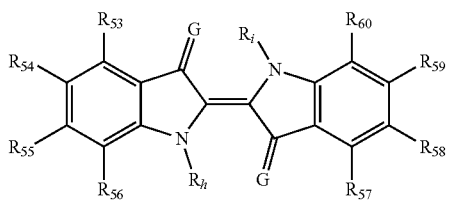

(XVII)

$R_{53}$, $R_{54}$, $R_{55}$, $R_{56}$, $R_{57}$, $R_{58}$, $R_{59}$ and $R_{60}$, which may be identical or different, represent a hydrogen atom or a group chosen from:
alkyl;
alkoxy, alkylthio;
hydroxyl, mercapto;
nitro, nitroso;
$R^\circ$—C(X)—X'—, $R^\circ$—X'—C(X)—, $R^\circ$—X'—C(X)—X"— with $R^\circ$ representing a hydrogen atom or an alkyl or aryl group; X, X' and X", which may be identical or different, representing an oxygen or sulfur atom, or NR with R representing a hydrogen atom or an alkyl group;
$(O)_2S(O^-)$—, $M^+$ with $M^+$ representing a hydrogen atom or a cationic counterion;
$(O)CO^-$—, $M^+$ with $M^+$ as defined previously;
G represents an oxygen or sulfur atom or a group NRe with Re as defined previously; in particular, G represents an oxygen atom;
Ri and Rh, which may be identical or different, represent a hydrogen atom or an alkyl group; it being understood that formula (XVII) comprises at least one sulfonate radical $(O)_2S(O^-)$—, $M^+$ or one carboxylate radical —$C(O)O^-$, $M^+$; preferentially sodium sulfonate.

As examples of dyes of formula (XVII), mention may be made of: Acid Blue 74;

g) the quinoline-based dyes of formula (XVIII):

[Chem. 35]

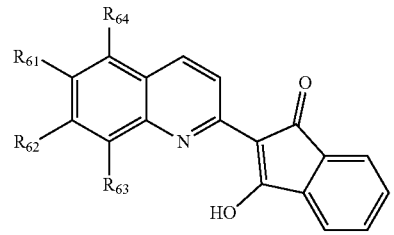

(XVIII)

$R_{61}$ represents a hydrogen or halogen atom or an alkyl group;

$R_{62}$, $R_{63}$ and $R_{64}$, which may be identical or different, represent a hydrogen atom or a group $(O)_2S(O^-)$—, $M^+$ with $M^+$ representing a hydrogen atom or a cationic counterion; or alternatively $R_{61}$ with $R_{62}$, or $R_{61}$ with $R_{64}$, together form a benzo group optionally substituted with one or more groups $(O)_2S(O^-)$—, $M^+$ with $M^+$ representing a hydrogen atom or a cationic counterion;

it being understood that formula (XVIII) comprises at least one sulfonate radical $(O)_2S(O^-)$—, $M^+$, preferentially sodium sulfonate.

As examples of dyes of formula (XVIII), mention may be made of: Acid Yellow 2, Acid Yellow 3 and Acid Yellow 5.

Among the natural direct dyes that may be used according to the invention, mention may be made of lawsone, juglone, alizarin, purpurin, carminic acid, kermesic acid, purpurogallin, protocatechaldehyde, indigo, isatin, curcumin, spinulosin, apigenidin and oreceins. Use may also be made of extracts or decoctions comprising these natural dyes and notably henna-based poultices or extracts.

Preferably, the direct dyes are chosen from anionic direct dyes.

The composition(s) used in the process according to the invention may comprise one or more pigments present in a total content ranging from 0.05% to 30% by weight, preferably from 0.1% to 20% by weight and better still from 0.1% to 15% by weight relative to the total weight of the composition.

The composition(s) used in the process according to the invention may comprise one or more direct dyes present in a total content ranging from 0.001 to 10% by weight, preferably from 0.005% to 5% by weight relative to the total weight of the composition.

The composition(s) used in the process according to the invention may comprise water. Preferably, water is present in a content ranging from 0.1% to 90% by weight, more preferentially from 0.5% to 88% by weight relative to the total weight of the composition.

The composition(s) used in the process according to the invention may comprise less than 2% by weight of water relative to the total weight of the composition.

According to one preferred embodiment of the invention, the composition(s) is(are) free from water (zero content). The water is not added during the preparation of the composition, but corresponds to the residual water provided by the mixed ingredients.

Oils

The process according to the invention may use one or more composition(s) comprising one or more oil(s).

The term "oil" is intended to mean a fatty substance that is liquid at ambient temperature (25° C.) and at atmospheric pressure (760 mmHg or $1.013 \times 10^5$ Pa).

The oil may be volatile or nonvolatile.

The term "volatile oil" refers to an oil that can evaporate on contact with the skin in less than one hour, at ambient temperature and atmospheric pressure. The volatile oil is a cosmetic volatile oil, which is liquid at ambient temperature. More specifically, a volatile oil has an evaporation rate of between 0.01 and 200 mg/cm$^2$/min, limits included (see protocol for measuring the evaporation rate indicated in the text below).

The term "nonvolatile oil" means an oil that remains on the skin or the keratin fiber at ambient temperature and atmospheric pressure. More specifically, a nonvolatile oil has an evaporation rate of strictly less than 0.01 mg/cm$^2$/min (see protocol for measuring the evaporation rate indicated in the text below).

Preferably, the composition(s) comprise(s) one or more volatile oil(s), more preferentially chosen from alkanes, silicones and mixtures thereof.

Even more preferentially, the composition(s) comprise(s) one or more volatile oil(s) chosen from $C_6$-$C_{16}$ alkanes, linear or cyclic volatile silicone oils, and mixtures thereof.

As regards the $C_6$-$C_{16}$ alkanes, they may be linear or branched, and possibly cyclic.

Mention may notably be made of branched $C_8$-$C_{16}$ alkanes, such as $C_8$-$C_{16}$ isoalkanes (also known as isoparaffins), isododecane, isodecane or isohexadecane, and for example the oils sold under the Isopar or Permethyl trade names, and mixtures thereof.

Mention may also be made of linear alkanes, preferably of plant origin, comprising from 7 to 15 carbon atoms, in particular from 9 to 14 carbon atoms and more particularly from 11 to 13 carbon atoms.

As examples of linear alkanes that are suitable for use in the invention, mention may be made of n-heptane (C7), n-octane (C8), n-nonane (C9), n-decane (C10), n-undecane (C11), n-dodecane (C12), n-tridecane (C13), n-tetradecane (C14) and n-pentadecane (C15), and mixtures thereof, and in particular the mixture of n-undecane (C11) and n-tridecane (C13) described in Example 1 of patent application WO 2008/155 059 by the company Cognis.

Mention may also be made of n-dodecane (C12) and n-tetradecane (C14) sold by Sasol under the references, respectively, Parafol 12-97 and Parafol 14-97, and also mixtures thereof.

As examples of alkanes that are suitable for use in the invention, mention may be made of the alkanes described in patent applications WO 2007/068 371 and WO 2008/155 059. These alkanes are obtained from fatty alcohols, which are themselves obtained from coconut kernel oil or palm oil.

According to one preferred embodiment, the composition(s) comprise(s) isododecane. Such a compound is, for example, the isododecane sold under the reference Isododecane by Ineos.

Preferably, at least one of the compositions used in the process according to the invention comprises one or more oil(s) chosen from $C_8$-$C_{16}$ alkanes, more preferentially from isododecane, isohexadecane, tetradecane and/or mixtures thereof.

More preferentially, at least one of the compositions used in the process according to the invention comprises isododecane.

The composition(s) according to the invention may also comprise one or more volatile silicone oil(s) different than the amino silicones b) previously described.

As volatile silicone oils that may be used in the invention, mention may be made of linear or cyclic silicone oils with a viscosity at ambient temperature of less than 8 cSt and in particular containing from 2 to 7 silicon atoms, these silicones optionally comprising alkyl or alkoxy groups containing from 1 to 10 carbon atoms.

As volatile silicone oils that may be used in the invention, mention may be made in particular of cyclopentasiloxane, octamethylcyclotetrasiloxane, decamethylcyclopentasiloxane, dodecamethylcyclohexasiloxane, heptamethylhexyltrisiloxane, heptamethyloctyltrisiloxane, hexamethyldisiloxane, octamethyltrisiloxane, decamethyltetrasiloxane and dodecamethylpentasiloxane, and mixtures thereof.

The composition(s) according to the invention may comprise one or more oils present in a total amount of between 5% and 99% by weight, preferably between 20% and 95% by weight and better still between 30% and 90% by weight, relative to the total weight of the composition.

Additives:

The process according to the invention may use one or more composition(s) containing any adjuvant or additive normally used.

Among the additives that may be contained in the composition(s), mention may be made of reducing agents, thickeners, softeners, antifoams, moisturizers, UV-screening agents, peptizers, solubilizers, fragrances, anionic, cationic, nonionic or amphoteric surfactants, silicone surfactants, proteins, vitamins, polymers, preserving agents, waxes and mixtures thereof.

The composition(s) according to the invention may notably be in the form of a suspension, a dispersion, a gel, an emulsion, notably an oil-in-water (O/W) or water-in-oil (W/O) emulsion, or a multiple emulsion (W/O/W or polyol/O/W or O/W/O), in the form of a cream, a mousse, a stick, a dispersion of vesicles, notably of ionic or nonionic lipids, a two-phase or multi-phase lotion, an anhydrous liquid or an anhydrous gel.

Those skilled in the art may select the appropriate presentation form, and also the method for preparing it, on the basis of his general knowledge, taking into account firstly the nature of the constituents used, notably their solubility in the support, and secondly the intended application of the composition.

According to one preferred embodiment, the process according to the invention uses a) at least one silicone comprising at least one carboxylic acid anhydride group of formula (I) as described previously, b) at least one amino silicone as described previously, and c) at least one coloring agent chosen from pigments, direct dyes and mixtures thereof, the compounds a), b) and c) being applied together or separately, in one or more compositions.

According to one more preferred embodiment, the process according to the invention uses a) at least one silicone comprising at least one carboxylic acid anhydride group of formula (III) as described previously, b) at least one amino silicone of formula (C) as described previously, and c) at least one pigment, the compounds a), b) and c) being applied together or separately, in one or more compositions.

Process for Treating Keratin Fibers

The present invention also relates to a process for cosmetically treating, in particular dyeing, keratin fibers such as the hair, implementing:

a1) a step of treating said fibers by application to the keratin fibers of a composition (A) comprising b) at least one amino silicone as previously described;
b1) optionally a washing, rinsing, drying and/or wringing out step; and
c1) a step of treating by application to the keratin fibers of a composition (B) comprising a) at least one silicone comprising at least one carboxylic acid anhydride group as previously described;
the composition (A) and/or the composition (B) comprising c) at least one coloring agent chosen from pigments, direct dyes and mixtures thereof as described previously;
it being understood that steps a1), b1) and c1) are carried out successively a1), then b1) then c1) or else c1), then b1), then a1) or else steps a1) and c1) being carried out together followed by b1).

Preferably, the composition (A) and/or the composition (B) comprise one or more oils as defined previously.

The composition (A) and/or the composition (B) can be used on wet or dry keratin fibers, and also on any type of fair or dark, natural or dyed, permanent-waved, bleached or relaxed fibers.

According to a particular embodiment of the process of the invention, the fibers are washed before applying the composition (A) and/or the composition (B) described above.

The application of the composition (A) and/or the composition (B) to the keratin fibers may be carried out by any conventional means, in particular using a comb, a fine brush, a coarse brush or with the fingers.

The dyeing process, i.e. application of the composition (A) and of the composition (B) to the keratin fibers, is generally carried out at ambient temperature (between 15 and 25° C.).

Preferably, after applying the composition (A) and the composition (B) to the keratin fibers, there is a waiting time of between 1 minute and 6 hours, in particular between 10 minutes and 5 hours, more particularly between 30 minutes and 4 hours, and more preferentially about 1 hour.

According to one preferred embodiment, the composition (A) as defined previously is applied to the dry or wet keratin fibers, then the keratin fibers are washed, rinsed and/or dried, then the composition (B) as defined previously is applied, then, optionally, said fibers are washed, rinsed and/or dried.

According to another preferred embodiment, the composition (B) as defined previously is applied to the dry or wet keratin fibers, then the keratin fibers are washed, rinsed and/or dried, then the composition (A) as defined previously is applied, then, optionally, said fibers are washed, rinsed and/or dried.

According to one particular embodiment, the composition (A) as defined previously and the composition (B) as defined previously are mixed, before applying the mixture to the keratin fibers, then optionally washing, rinsing and/or drying said fibers.

According to one particular embodiment, a composition (C) comprising a) at least one silicone comprising at least one carboxylic acid anhydride group as defined previously, b) at least one amino silicone as described previously and c) at least one coloring agent chosen from pigments, direct dyes and mixtures thereof, as described previously, is applied to the keratin fibers, then said keratin fibers are optionally washed, rinsed and/or dried.

Preferably, the composition (A) and/or the composition (B) are applied to dry keratin fibers.

The drying step may last from 5 to 20 minutes, preferably from 5 to 15 minutes.

The process according to the invention may comprise a step of applying heat to the keratin fibers using a heating tool.

The heat application step of the process of the invention may be performed using a hood, a hairdryer, a straightening iron, a curling iron, a Climazon, etc.

Preferably, the heat application step of the process of the invention is carried out using a hairdryer and/or a straightening iron.

When the process of the invention involves a step of applying heat to the keratin fibers, the step of applying heat to the keratin fibers takes place after applying the composition (A) and/or the composition (B) to the keratin fibers.

During the step of applying heat to the keratin fibers, a mechanical action may be exerted on the locks, such as combing, brushing or running the fingers through.

When the step of applying heat to the keratin fibers is performed using a hood or a hairdryer, the temperature is preferably between 30° C. and 110° C., preferentially between 50° C. and 90° C.

When the step of applying heat to the keratin fibers is performed using a straightening iron, the temperature is preferably between 110° C. and 220° C., preferably between 140° C. and 200° C.

When the step of applying heat to the keratin fibers is carried out using a straightening iron, the keratin fibers are dry.

In a particular variant, the process of the invention involves a step (d'1) of applying heat using a hood, a hairdryer or a Climazon, preferably a hairdryer, and a step (d'2) of applying heat using a straightening or curling iron, preferably a straightening iron.

Step (d' 1) may be carried out before step (d2').

During step (d'1), also referred to as the drying step, the fibers may be dried, for example at a temperature above or equal to 30° C. According to one particular embodiment, this temperature is above 40° C. According to a particular embodiment, this temperature is above 45° C. and below 110° C.

Preferably, if the fibers are dried, they are dried, in addition to a supply of heat, with a flow of air. This flow of air during drying makes it possible to improve the strand separation of the coating.

During drying, a mechanical action may be exerted on the locks, such as combing, brushing or running the fingers through.

During step (d'2), the passage of the straightening or curling iron, preferably the straightening iron, may be carried out at a temperature ranging from 110° C. to 220° C., preferably between 140° C. and 200° C.

After the step of treatment with the composition (B) as defined previously, the keratin fibers are generally dried at a temperature ranging from 50 to 90° C.

After the step of treatment with the composition (B) as defined previously, the keratin fibers may be rinsed with water, and optionally washed with a shampoo and then rinsed with water, before being dried or left to dry.

Preferably, the step of washing the keratin fibers with a shampoo is carried out 24 h after the application of the composition (B) to the keratin fibers.

The present invention also relates to a process for treating keratin fibers such as the hair, comprising the following steps:
a1) applying, to the keratin fibers, a) at least one silicone comprising at least one carboxylic acid anhydride group as described previously, b) at least one amino silicone as described previously, and c) at least one coloring agent chosen from pigments, direct dyes and mixtures thereof, the compounds a), b) and c) being applied together or separately, in one or more compositions, and b1) applying to the dyed keratin fibers a makeup-removing composition (D) comprising at least one hydrocarbon-based oil.

Thus, the process according to the invention may comprise a step of applying a makeup-removing composition to dyed keratin fibers such as the hair. This step may take place following the dyeing of the keratin fibers with composition(s) according to the invention, after the optional step of applying heat to the keratin fibers, or after a defined time, i.e. days or weeks, after the application of the dye composition(s) to the keratin fibers and the optional step of applying heat to the keratin fibers.

The makeup-removing composition may correspond to a makeup-removing composition conventionally used in cosmetics. The makeup-removing composition comprises at least one hydrocarbon-based oil.

Preferably, the hydrocarbon-based oil(s) are chosen from synthetic esters of formula $R_1COOR_2$ wherein $R_1$ represents a fatty acid residue including from 8 to 29 carbon atoms, and $R_2$ represents a branched or unbranched hydrocarbon-based chain containing from 3 to 30 carbon atoms, and mixtures thereof, more preferentially from isopropyl myristate, isononyl isononanoate and/or mixtures thereof.

Preferably, the application of the composition(s) as described above to keratin fibers such as the hair is carried out before the application of the makeup-removing composition (D).

The step of applying heat to the keratin fibers may be performed after the application of the dye composition and before the application of the makeup-removing composition to the keratin fibers.

The makeup-removing composition may be applied to keratin fibers dyed with the dye composition(s) according to the invention as defined previously.

The application of the makeup-removing composition may be performed on dry dyed keratin fibers or wet dyed keratin fibers and also on all types of fibers.

The makeup-removing process is generally performed at ambient temperature (between 15° C. and 25° C.).

The application of the makeup-removing composition may be performed immediately after the application of the dye composition(s) (i.e. a few minutes to a few hours after the application of the dye composition(s)), or in the days or weeks following the application of the dye composition(s).

The makeup-removing composition may be applied with the aid of any suitable support, which is notably capable of absorbing it, for example a fibrous makeup-removing disk, for example a woven or nonwoven fabric, cotton wool, a flocked film, a sponge, a wipe, or a twisted or injection-molded mascara application brush.

The makeup-removing composition may be contained in a container and taken up gradually each time makeup is removed. As a variant, the makeup-removing composition impregnates the support used for makeup removal, the support possibly being packaged, in this case, for example in leaktight packaging.

After the makeup-removing composition has been used, it is possible for the keratin fibers to be not rinsed. As a variant, they may be rinsed. The rinsing may be performed, for example, with running water, without addition of a soap.

The present invention also relates to a multi-compartment device comprising:

a first compartment containing a composition (A) comprising b) at least one amino silicone as described previously;

a second compartment containing a composition (B) comprising a) at least one silicone comprising at least one carboxylic acid anhydride group as described previously;

and optionally a third compartment containing a makeup-removing composition (D) comprising at least one hydrocarbon-based oil as described previously;

the composition (A) and/or the composition (B) comprising c) at least one coloring agent chosen from pigments, direct dyes and mixtures thereof.

The present invention will now be described more specifically by means of examples, which do not in any way limit the scope of the invention. However, the examples make it possible to support specific features, variants and preferred embodiments of the invention.

EXAMPLE

Example 1

Composition Base Coat: Compositions (g/100 g)

TABLE 1

| Compositions | A | B |
|---|---|---|
| Amodimethicone (KF-8004 sold by the company Shin Etsu) | 5 | 5 |
| Pigment (red iron oxide) | 5 | 5 |
| Cetyl PEG/PPG-10/1 dimethicone (Abil EM 90 sold by the company Evonik Goldschmidt) | — | 1 |
| Isododecane | qs 100 | 10 |
| Water | — | qs 100 |

Composition Top Coat: Compositions (g/100 g)

TABLE 2

| Compositions | C | D |
|---|---|---|
| Silicone comprising at least one carboxylic acid anhydride group (X-22-168A sold by the company Shin Etsu) | 5 | 5 |
| Cetyl PEG/PPG-10/1 dimethicone (Abil EM 90 sold by the company Evonik Goldschmidt) | — | 1 |
| Isododecane | qs 100 | 6 |
| Water | — | qs 100 |

Protocol:

Compositions A and B according to the invention (base coat compositions) are applied respectively to locks of natural dry hair containing 90% gray hairs, in a proportion of 0.5 g of composition per gram of lock.

The locks of hair are then combed and dried with a hairdryer.

Compositions C and D according to the invention (top coat compositions) are then applied respectively to said locks of dry hair, in a proportion of 0.5 g of composition per gram of lock.

The locks of hair are then combed and dried with a hairdryer. The locks of hair are left at ambient temperature for 24 hours.

The locks of hair have a natural feel and can be separated with the fingers or by using a comb and/or a brush.

The locks of hair thus dyed are then subjected to a test of several repeated shampoo washes so as to evaluate the resistance (persistence) of the coloring obtained with respect to shampoo washing.

Shampoo wash protocol:

The locks are washed with a standard shampoo (Garnier Ultra Doux) respectively at T=24 h.

The locks of hair are then rinsed, combed and dried with a hairdryer.

The next shampoo wash is then performed on the locks thus dried.

Results:

The persistence of the color of the locks was evaluated in the CIE L*a*b* system, using a Minolta Spectrophotometer CM3600D colorimeter (illuminant D65, angle 10°, specular component included).

In this L*a*b* system, L* represents the intensity of the color, a* indicates the green/red color axis and b* the blue/yellow color axis.

The persistence of the coloring is evaluated by the color difference ΔE between the dyed locks before shampooing, then after having undergone 2, 5, 10 and 20 shampoo washes according to the protocol described above. The lower the ΔE value, the more persistent the color with respect to shampoo washing.

The ΔE value is calculated according to the following equation:

$$\Delta E = \sqrt{(L^* - L_0^*)^2 + (a^* - a_0^*)^2 + (b^* - b_0^*)^2} \quad [\text{Math. 1}]$$

In this equation, L*a*b* represent the values measured after dyeing the hair and after performing the shampoo washes, and $L_0^* a_0^* b_0^*$ represent the values measured after dyeing the hair but before shampoo washing.

TABLE 3

| Compositions | Number of shampoo washes | L* | a* | b* | ΔE |
|---|---|---|---|---|---|
| Compositions A + C | 0 | 39.49 | 22.48 | 18.41 | — |
| | 2 | 38.52 | 25.07 | 21.51 | 4.15 |
| | 5 | 42.79 | 18.73 | 16.92 | 5.21 |
| | 10 | 48.04 | 17.13 | 18.15 | 10.09 |
| | 20 | 54.96 | 10.69 | 16.79 | 19.52 |
| Compositions B + D | 0 | 37.54 | 32.81 | 28.53 | — |
| | 2 | 40.38 | 32.56 | 28.82 | 2.87 |
| | 5 | 38.69 | 31.38 | 27.03 | 2.37 |
| | 10 | 43.35 | 29.1 | 25.25 | 7.63 |
| | 20 | 47.92 | 23.1 | 21.47 | 15.87 |

The locks of hair dyed with the compositions A+C or with the compositions B+D according to the invention and washed with two, five, ten or twenty shampoo washes have low ΔE values.

Thus, the colored coating of the keratin fibers obtained with compositions A+C or with compositions B+D according to the invention shows good persistence with respect to shampoo washing. Indeed, the locks of hair dyed with the compositions A+C or with the compositions B+D according to the invention and washed with two, five, ten or twenty shampoo washes have good color persistence.

Example 2

Composition Base Coat: Compositions (g/100 g)

TABLE 4

| Compositions | B |
|---|---|
| Amodimethicone (KF-8004 sold by the company Shin Etsu) | 5 |
| Pigment (red iron oxide) | 5 |
| Cetyl PEG/PPG-10/1 dimethicone (Abil EM 90 sold by the company Evonik Goldschmidt) | 1 |
| Isododecane | 10 |
| Water | qs 100 |

Composition Top Coat: Compositions (g/100 g) AM: Active Material

TABLE 5

| Compositions | D1 (invention) | D2 (comparative) |
|---|---|---|
| Silicone comprising at least one carboxylic acid anhydride group (X-22-168A sold by the company Shin Etsu) | 5 am | — |
| Dimethicone PEG-7 phosphate (Silsense PE-200L Silicone sold by the company Lubrizol) | — | 5 am |
| Cetyl PEG/PPG-10/1 dimethicone (Abil EM 90 sold by the company Evonik Goldschmidt) | 1 | 1 |
| Isododecane | 6 | 6 |
| Water | qs 100 | qs 100 |

Protocol:

Composition B (base coat composition) is applied respectively to locks of natural dry hair containing 90% gray hairs, in a proportion of 0.5 g of composition per gram of lock.

The locks of hair are then combed and dried with a hairdryer.

Composition D1 according to the invention and comparative composition D2 (top coat compositions) are then applied respectively to said locks of dry hair, in a proportion of 0.5 g of composition per gram of lock.

The locks of hair are then combed and dried with a hairdryer. The locks of hair are left at ambient temperature for 24 hours.

The locks of hair have a natural feel and can be separated with the fingers or by using a comb and/or a brush.

The locks of hair thus dyed are then subjected to a test of several repeated shampoo washes so as to evaluate the resistance (persistence) of the coloring obtained with respect to shampoo washing.

The Shampoo wash protocol is the same as the one described in example 1.

Results:

The persistence of the color of the locks was evaluated in the CIE L*a*b* system, using a Minolta Spectrophotometer CM3600D colorimeter (illuminant D65, angle 10°, specular component included).

In this L*a*b* system, L* represents the intensity of the color, a* indicates the green/red color axis and b* the blue/yellow color axis.

The persistence of the coloring is evaluated by the color difference ΔE between the dyed locks before shampooing, then after having undergone 3 shampoo washes according to the protocol described in example 1. The lower the ΔE value, the more persistent the color with respect to shampoo washing.

The ΔE value is calculated according to the following equation:

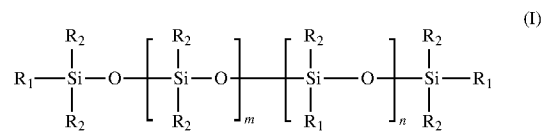

$$\Delta E = \sqrt{(L^* - L_0^*)^2 + (a^* - a_0^*)^2 + (b^* - b_0^*)^2} \quad \text{[Math. 2]}$$

In this equation, L*a*b* represent the values measured after dyeing the hair and after performing the shampoo washes, and $L_0^* a_0^* b_0^*$ represent the values measured after dyeing the hair but before shampoo washing.

TABLE 3

| Compositions | Number of shampoo washes | L* | a* | b* | ΔE |
|---|---|---|---|---|---|
| Compositions B + D1 (invention) | 0 | 37.26 | 31 | 25.48 | — |
| | 3 | 38.53 | 28.88 | 23.22 | 3.35 |
| Compositions B + D2 (comparative) | 0 | 36.69 | 29.02 | 23.56 | — |
| | 3 | 63.6 | 3.97 | 17.06 | 37.33 |

The locks of hair dyed with the compositions B+D1 according to the invention and washed with three shampoo washes have lower ΔE values than the locks of hair dyed with the comparative composition B+D2.

Thus, the colored coating of the keratin fibers obtained with compositions B+D1 according to the invention shows good persistence with respect to shampoo washing. Indeed, the locks of hair dyed with compositions B+D1 according to the invention and washed with three shampoo washes have better persistence of the color than the locks of hair dyed with the comparative composition B+D2.

The invention claimed is:

1. A process for treating keratin fibers, comprising: applying to the keratin fibers:
   a) at least one silicone comprising at least one carboxylic acid anhydride group,
   b) at least one amino silicone; and
   c) at least one coloring agent chosen from pigments, direct dyes and mixtures thereof,
   wherein the a) at least one silicone, b) at least one amino silicone, and c) at least one coloring agent are applied to the keratin fibers, together or separately, in one or more compositions.

2. The process of claim 1, wherein the at least one silicone comprising at least one carboxylic acid anhydride group chosen from organosiloxanes of formula (I):

wherein:
R₁ is independently chosen from an alkyl group containing from 1 to 20 carbon atoms, optionally substituted with at least one group chosen from a hydroxyl group (OH) or a thiol group (SH); a cycloalkyl group containing from 3 to 20 carbon atoms; an alkoxy group containing from 1 to 2 carbon atoms; an aryl group containing from 6 to 12 carbon atoms, optionally substituted with at least one group chosen from a hydroxyl group (OH) or a thiol group (SH) or a group of formula (II):

wherein R₃ represents an alkyl group containing from 1 to 4 carbon atoms;
p denotes an integer ranging from 0 to 4;
R₂ is independently chosen from an alkyl group containing from 1 to 20 carbon atoms, optionally substituted with at least one group chosen from a hydroxyl group (OH) or a thiol group (SH); a cycloalkyl group containing from 3 to 20 carbon atoms; an alkoxy group containing from 1 to 2 carbon atoms; an aryl group containing from 6 to 12 carbon atoms, optionally substituted with at least one group chosen from a hydroxyl group (OH) or a thiol group (SH);
m denotes an integer ranging from 1 to 10; and
n denotes an integer ranging from 1 to 50;
wherein at least one of the radicals R₁ represents a group of formula (II).

3. The process of claim 1, wherein the at least one silicone comprising at least one carboxylic acid anhydride group is chosen from organosiloxanes of formula (III):

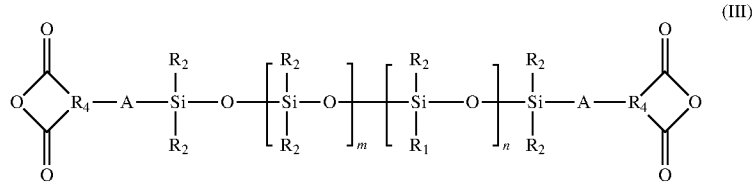

wherein:

$R_1$ is independently chosen from an alkyl group containing from 1 to 20 carbon atoms, optionally substituted with at least one group chosen from a hydroxyl group (OH) or a thiol group (SH); a cycloalkyl group containing from 3 to 20 carbon atoms; an alkoxy group containing from 1 to 2 carbon atoms; an aryl group containing from 6 to 12 carbon atoms, optionally substituted with at least one group chosen from a hydroxyl group (OH) or a thiol group (SH) or a group of formula (II):

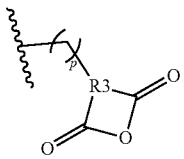

(II)

wherein $R_3$ represents an alkyl group containing from 1 to 4 carbon atoms;

p denotes an integer ranging from 0 to 4;

$R_2$ is independently chosen from an alkyl group containing from 1 to 20 carbon atoms, optionally substituted with at least one group chosen from a hydroxyl group (OH) or a thiol group (SH); a cycloalkyl group containing from 3 to 20 carbon atoms; an alkoxy group containing from 1 to 2 carbon atoms; an aryl group containing from 6 to 12 carbon atoms, optionally substituted with at least one group chosen from a hydroxyl group (OH) or a thiol group (SH);

$R_4$ represents an alkyl group containing from 1 to 4 carbon atoms;

A represents an alkylene group containing from 1 to 4 carbon atoms;

m denotes an integer ranging from 1 to 10; and n denotes an integer ranging from 1 to 50.

4. The process of claim 1, wherein the at least one silicone comprising at least one carboxylic acid anhydride group is chosen from organosiloxanes of formula (IV):

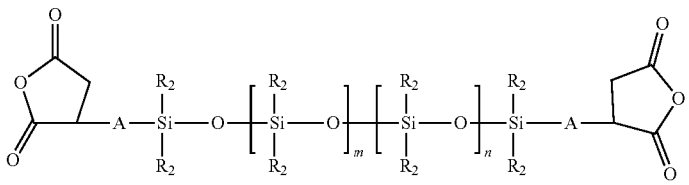

wherein:

$R_2$ is independently chosen from an alkyl group containing from 1 to 20 carbon atoms, optionally substituted with at least one group chosen from a hydroxyl group (OH) or a thiol group (SH); a cycloalkyl group containing from 3 to 20 carbon atoms; an alkoxy group containing from 1 to 2 carbon atoms; an aryl group containing from 6 to 12 carbon atoms, optionally substituted with at least one group chosen from a hydroxyl group (OH) or a thiol group (SH);

A represents an alkylene group containing from 1 to 4 carbon atoms;

m denotes an integer ranging from 1 to 10; and n denotes an integer ranging from 1 to 50.

5. The process of claim 1, wherein the one or more compositions used in the process comprise the at least one silicone comprising at least one carboxylic acid anhydride group in a total amount ranging from 0.1% to 40% by weight, relative to the total weight of the composition.

6. The process of claim 1, wherein the at least one amino silicone is chosen from amino silicones corresponding to formula (B):

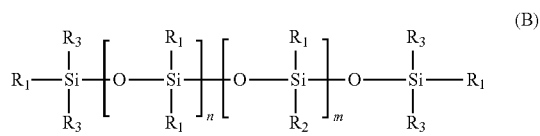

wherein:

$R_1$ is independently chosen from a hydrogen atom, a phenyl group, a hydroxyl group, a $C_1$-$C_8$ alkyl group;

$R_2$ represents a monovalent radical of formula -$C_qH_{2q}$L wherein q is a number ranging from 2 to 8 and L is an optionally quaternized amino group chosen from:

—N(R")$_2$;  —N$^+$(R")$_3$A$^-$;  —NR"—Q—N(R")$_2$  and —NR"—Q—N$^+$(R")$_3$A$^-$, wherein R" is independently chosen from a hydrogen atom, a phenyl group, a benzyl group or a saturated monovalent hydrocarbon-based radical; Q denotes a linear or branched group of formula $C_rH_{2r}$, r being an integer ranging from 2 to 6; and A$^-$ represents a cosmetically acceptable anion comprising a halide;

$R_3$ is independently chosen from a $C_1$-$C_8$ alkyl group, or a monovalent radical of formula —$C_qH_{2q}$L wherein q is a number ranging from 2 to 8 and L is an optionally quaternized amine group chosen from:

—N(R")$_2$;  —N$^+$(R")$_3$A$^-$;  —NR"—Q—N(R")$_2$  and —NR"—Q—N$^+$(R")$_3$A$^-$, wherein R" is independently chosen from a hydrogen atom, a phenyl group, a benzyl group or a saturated monovalent hydrocarbon-based radical;

Q denotes a linear or branched group of formula $C_rH_{2r}$, r being an integer ranging from 2 to 6; and A$^-$ represents a cosmetically acceptable anion comprising a halide; and m and n are numbers such that the sum (n+m) ranges from 1 to 2000, wherein m denotes a number from 0 to 1999, and n denotes a number from 1 to 2000.

7. The process of claim 6, wherein the at least one amino silicone is chosen from amino silicones corresponding to formula (C):

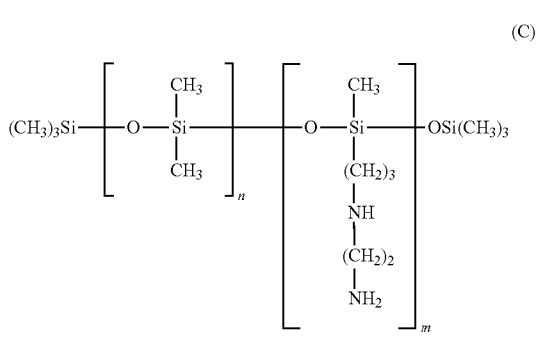

wherein m and n are numbers such that the sum (n+m) ranges from 1 to 2000.

8. The process of claim 1, wherein the at least one amino silicone is present in a total amount ranging from 0.01% to 20% by weight, relative to the total weight of the one or more compositions.

9. The process of claim 1, wherein at least one of the one or more compositions comprises one or more oils.

10. The process of claim 9, wherein the one or more oils are chosen from $C_8$-$C_{16}$ alkanes.

11. The process of claim 1, wherein the at least one coloring agent is present in a total amount ranging from 0.05% to 30% by weight, relative to the total weight of the one or more compositions.

12. A process for cosmetically treating keratin fibers, comprising:
  applying to the keratin fibers a composition (A) comprising at least one amino silicone;
  optionally washing, rinsing, drying and/or wringing out the keratin fibers; and
  applying to the keratin fibers a composition (B) comprising at least one silicone comprising at least one carboxylic acid anhydride group;
    wherein at least one of the composition (A) or the composition (B) comprises at least one coloring agent chosen from pigments, direct dyes and mixtures thereof,
    wherein the at least one amino silicone, the at least one silicone, and the at least one coloring agent are applied to the keratin fibers, together or separately, in one or more compositions.

13. The process of claim 1, further comprising applying to the keratin fibers a makeup-removing composition comprising at least one hydrocarbon-based oil.

14. The process as claimed in claim 13, wherein the application of the one or more compositions to the keratin fibers is carried out before the application of the makeup-removing composition.

15. A multi-compartment device comprising:
  a first compartment containing a composition (A) comprising at least one amino silicone;
  a second compartment containing a composition (B) comprising at least one silicone comprising at least one carboxylic acid anhydride group;
  and optionally a third compartment containing a makeup-removing composition (D) comprising at least one hydrocarbon-based oil;
  wherein at least one of the composition (A) or the composition (B) comprises at least one coloring agent chosen from pigments, direct dyes and mixtures thereof.

* * * * *